(12) United States Patent
Sasse et al.

(10) Patent No.: US 10,653,545 B2
(45) Date of Patent: May 19, 2020

(54) SLEEVE TUBE AND METHOD OF USE

(71) Applicant: Kent C. Sasse, Reno, NV (US)

(72) Inventors: Kent C. Sasse, Reno, NV (US); Matthew T. Fisher, Reno, NV (US)

(73) Assignee: Kent C. Sasse, Reno, NV (US)

( * ) Notice: Subject to any disclaimer, the term of this patent is extended or adjusted under 35 U.S.C. 154(b) by 0 days.

(21) Appl. No.: 15/838,057

(22) Filed: Dec. 11, 2017

(65) Prior Publication Data
US 2018/0098871 A1    Apr. 12, 2018

Related U.S. Application Data

(63) Continuation-in-part of application No. 15/332,897, filed on Oct. 24, 2016, now abandoned.
(Continued)

(51) Int. Cl.
*A61M 1/00*    (2006.01)
*A61F 5/00*    (2006.01)
(Continued)

(52) U.S. Cl.
CPC .......... *A61F 5/0089* (2013.01); *A61F 5/0076* (2013.01); *A61M 1/008* (2013.01);
(Continued)

(58) Field of Classification Search
CPC .............. A61B 5/4238; A61M 1/0039; A61M 2010/1053; A61M 2210/105; A61M 25/10; A62M 2205/0266
See application file for complete search history.

(56) References Cited

U.S. PATENT DOCUMENTS

2007/0239138 A1  10/2007 Lawrence et al.
2007/0282356 A1  12/2007 Sonnenschein et al.
(Continued)

FOREIGN PATENT DOCUMENTS

WO    WO 2009027065    3/2009

OTHER PUBLICATIONS

International Search Report and Written Opinion of the International Searching Authority for International Application PCT/US18/47997, dated Oct. 26, 2018.
(Continued)

*Primary Examiner* — Kai H Weng
(74) *Attorney, Agent, or Firm* — Holland & Hart LLP

(57) ABSTRACT

Methods, systems, and devices are described for fabricating, providing, and using an orogastric tube. The orogastric tube may have, among other things: a proximal end section; a distal end section opposite the proximal end section and having a flexible, resilient curved portion; at least one sump channel extending from the proximal end section along a pre-determined length of the orogastric tube into the distal end section; at least one suction channel extending from the proximal end section along a pre-determined length of the orogastric tube into the distal end section; and optionally at least one balloon channel extending from the proximal end section along a pre-determined length of the orogastric tube to the distal end section. The optional balloon channel is in communication with an expandable balloon in the distal end section; and a main channel encloses a pre-determined length of the sump channel, the suction channel, and, if present, the balloon channel.

23 Claims, 20 Drawing Sheets

Related U.S. Application Data

(60) Provisional application No. 62/550,159, filed on Aug. 25, 2017, provisional application No. 62/245,524, filed on Oct. 23, 2015.

(51) Int. Cl.
*A61J 15/00* (2006.01)
*A61B 17/00* (2006.01)
*A61B 90/00* (2016.01)
*A61B 17/02* (2006.01)

(52) U.S. Cl.
CPC ....... *A61M 1/0088* (2013.01); *A61B 17/0218* (2013.01); *A61B 2017/00557* (2013.01); *A61B 2017/00566* (2013.01); *A61B 2090/061* (2016.02); *A61F 2005/0016* (2013.01); *A61J 15/0003* (2013.01); *A61J 15/0049* (2013.01); *A61J 15/0073* (2013.01); *A61M 2205/0266* (2013.01); *A61M 2207/00* (2013.01); *A61M 2210/105* (2013.01); *A61M 2210/1053* (2013.01)

(56) References Cited

U.S. PATENT DOCUMENTS

| | | |
|---|---|---|
| 2010/0010298 A1 | 12/2010 | Bakos et al. |
| 2012/0190938 A1* | 7/2012 | Addington ............. A61B 5/037 600/301 |
| 2014/0005647 A1* | 1/2014 | Shuffler ................. A61B 18/24 606/16 |
| 2015/0133857 A1* | 5/2015 | Rokde ................... A61F 5/0089 604/95.04 |
| 2015/0328031 A1* | 11/2015 | Rokde ................ A61M 25/007 600/104 |
| 2017/0112651 A1 | 4/2017 | Sasse et al. |

OTHER PUBLICATIONS

Fujiwara, et al.; Gastroesophageal Relux after distal gastrectomy: possible significance of the angle of His; American Journal of Gastroenterology; Issue 93; p. 11-15; (1998).

* cited by examiner

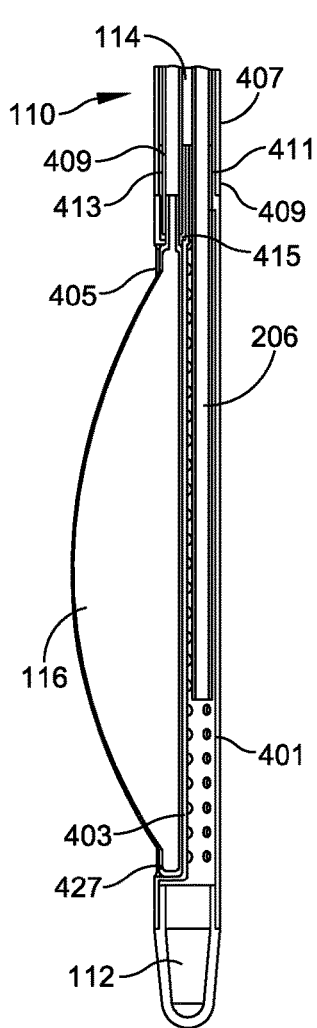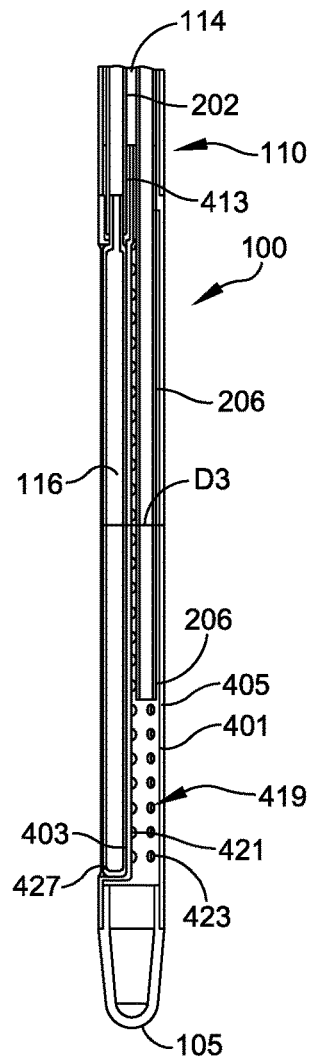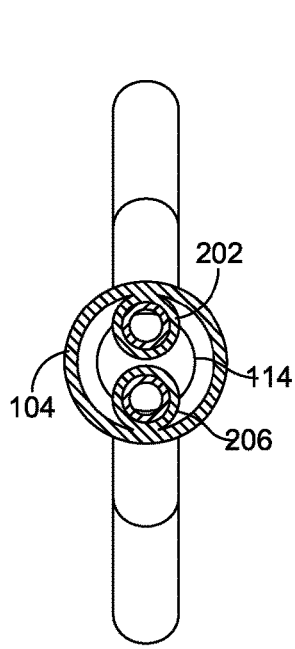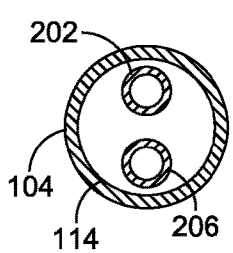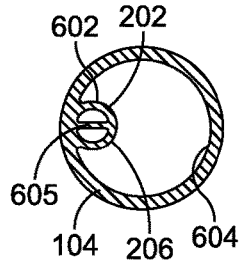
FIG. 4A  FIG. 4B  FIG. 5  FIG. 6A  FIG. 6B
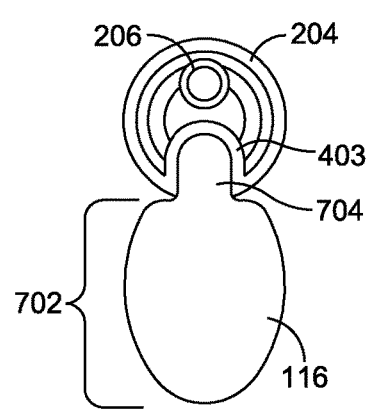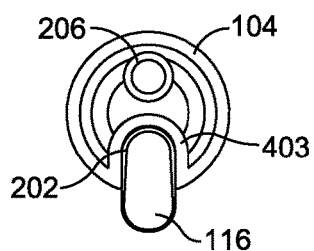
FIG. 7A  FIG. 7B

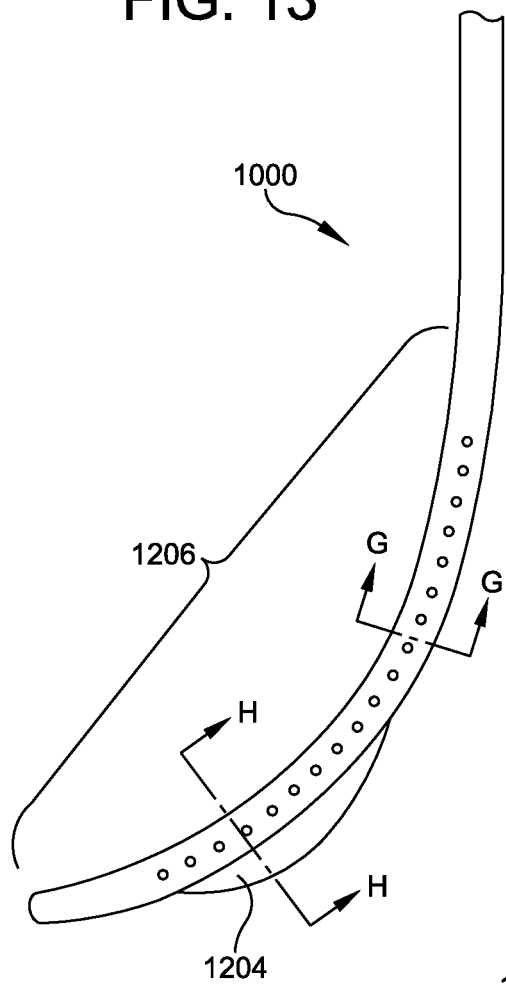
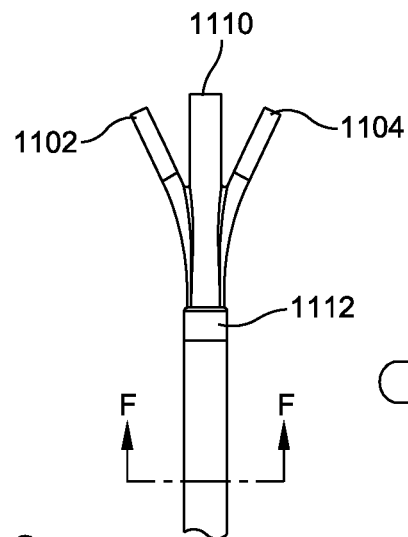
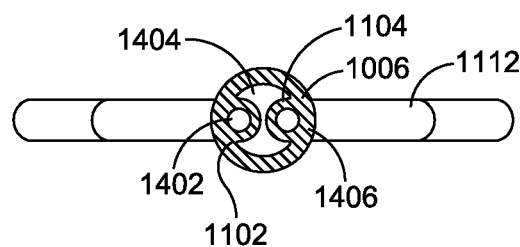
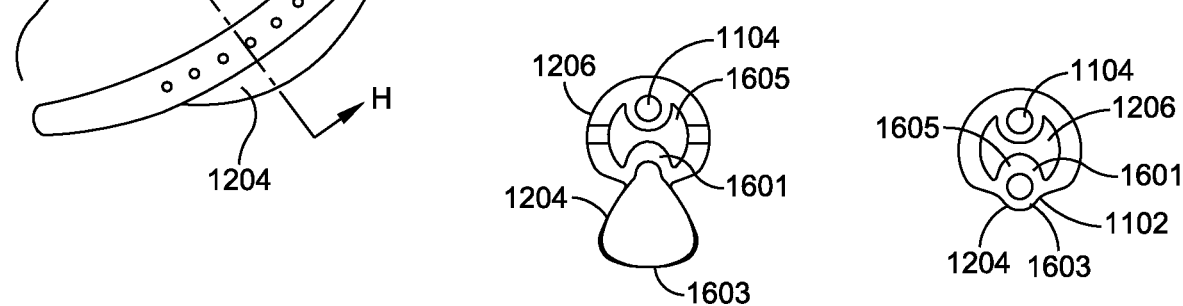
FIG. 13
FIG. 14
FIG. 15
FIG. 16A    FIG. 16B

SLEEVE TUBE AND METHOD OF USE

CROSS-REFERENCE TO RELATED APPLICATIONS

This application claims priority to the applicant's prior provisional patent application, titled Sleeve Tube and Method of Use, Ser. No. 62/550,159, filed Aug. 25, 2017, and the applicant's prior non-provisional patent application, titled Sleeve Tube and Method of Use, Ser. No. 15/332,897, filed Oct. 24, 2016, which claims priority through the applicant's prior provisional application, titled Sleeve Tube and Method of Use, Ser. No. 62/245,524, filed Oct. 23, 2015, all of which applications are incorporated by reference. In the event of any inconsistency, however, between any such application and this application, this application shall govern

FIELD OF THE DISCLOSURE

The present disclosure relates to an orogastric sleeve tube ("sleeve tube") and methods of use, and in one aspect relates to a multi-channel sleeve tube that may be used in laparoscopic sleeve gastrectomy surgery. The sleeve tube may combine unique features of a gastric aspiration tube utilizing sump technology in combination with a novel sizing calibration tube. In some embodiments, the sleeve tube may be used for gastrectomy surgeries for gastric tumors, and/or for other types of procedures such as, but not limited to, laparoscopic sleeve gastrectomy surgery, bariatric surgery, and endoscopic procedures.

BACKGROUND OF SOME ASPECTS OF THE DISCLOSURE

Sleeve gastrectomy surgery is one of the most frequently performed procedures for the treatment of morbid obesity with estimates that more than 200,000 gastrectomy procedures may be performed in the United States in the next year. In a gastrectomy procedure, the volume of the stomach into which food may pass and be processed is reduced. This reduction is commonly achieved by removing a large portion (commonly 75%) of the stomach and stapling the remaining portion of the stomach shut, providing a smaller residual food-processing portion of the stomach called the stomach sleeve.

With existing gastrectomy technology, operating room personnel use multiple separate tubes to pass through a patient's mouth and esophagus into the patient's stomach in order to perform gastric procedures. The procedure can involve (i) first inserting a standard tube, such as a nasogastric tube, having only a suction channel to inflate the stomach, evacuate the gastric contents from the patient's stomach, and deflate the stomach, (ii) removing the suction tube and inserting a separate, solid sizing calibration rod or bougie into the stomach to guide the cutting/stapling of the stomach adjacent the rod, to yield the residual stomach sleeve of reduced volume, and (iii) removal of the calibration rod insertion of a standard nasogastric tube into the stomach, to deflate the stomach perform a leak test by inserting colored dye into, and distending, the residual stomach. The multiple tube procedure is not only time consuming but also increases the risk of lengthier anesthesia, trauma to the patient during the procedure, and a resulting residual stomach sleeve that is unnaturally shaped and/or too narrow, and thus subject to risk of becoming twisted, called the "windsock deformity," or otherwise becoming blocked.

For example, one particularly serious type of gastrectomy patient trauma, esophageal perforation, is believed to occur in less than 0.03% of gastrectomy tube insertions. This type of trauma is, however, a gravely serious complication, resulting in mortality in over 20% of cases in which perforation occurs.

As another example, the windsock deformity occurs in approximately 1% of gastrectomy procedures, and postoperative stenosis or narrowing of the resulting stomach sleeve occurs in between 1% and 3% of cases of sleeve gastrectomy. Given that there hundreds of thousands of such procedures every year in the U.S., these complications present real and costly problems.

Existing sleeve tubes are typically straight and include, for example, the ViSiGi 3D tube from Boheringer Ingelheim (e.g., having a French ("Fr") gauge (or width) of 36 or 40). Straight sleeve tubes promote a straightening of the stomach, which can yield a less naturally shaped and unduly narrow stomach sleeve that is more prone to twisting, kinking, and obstructing.

The ViSiGi 3D tube also has only single channel that can become clogged prematurely by gastric contents during the gastrectomy procedure. When this occurs, the tube must be removed, cleared, and re-inserted into the patient to complete removal of gastric contents and deflation of the stomach.

Nasogastric Sump tube model number 0042140 from Bard Medical has two channels: a suction channel and a sump channel in material transfer communication with apertures in the working end section. Like most prior art gastrectomy tubes, this Bard Medical tube has a working end section that is straight, too narrow (from 10-18 Fr.) to provide a guide to help the physician calibrate the size of the residual stomach sleeve, and a blunt, relatively inflexible tip, which also can result in anatomical trauma to the patient during the gastrectomy procedure.

Consequently, existing tube technology typically fails to suction, aspirate, and deflate the stomach adequately, quickly, and with reduced risk of trauma to the patient during the procedure and afterwards, such as due to the windsock deformity and/or other complications due to an unnatural and/or excessively narrow shape of the residual stomach sleeve.

BRIEF SUMMARY OF SOME ASPECTS OF THE DISCLOSURE

The applicants believe they have discovered at least some of the problems and issues with the prior art noted above. They have therefore invented, among other features, a multi-channeled and/or curved sleeve tube for use in gastrectomies and other procedures. Other procedures may include, for example, surgeries for gastric tumors, bariatric surgery, and endoscopic procedures and other surgeries where a curved calibration tube can be utilized. Yet other procedures may be performed as described infra.

One aspect of the present disclosure provides a multi-channeled sleeve tube having two or more among a main channel, a sump channel, and a balloon channel extending through a body section of the sleeve tube. In some embodiments, the sleeve tube of the present disclosure can optionally combine features of multiple, independent tubes of the prior art, while at least also providing a curved or curvable working section adjacent the distal tip section or end of the sleeve tube.

In some embodiments, having one multi-channeled tube that performs multiple functions can eliminate or reduce the number of placements and removals of tubes into the patient's esophagus; and in some applications, reducing the number of placements can be particularly useful because each time a tube is introduced there is a risk of perforation, laceration, and injury to the tissues of the oropharynx and esophagus. By eliminating two or three passage procedures, in at least a substantial number of applications, complications to the patient can be significantly decreased, and cost savings can accrue because valuable operating room time can be saved.

In some embodiments, the distal end of the sleeve tube may have a series of perforations that may, in some instances, further enable evacuation of gastric contents as well as facilitate injection of fluid into the stomach such as during a dye leak test. Additionally, some embodiments of the sleeve tube of the present disclosure may provide a sump channel to vent or supply air or gas when using the sleeve tube.

Some embodiments have a balloon channel coupled to a dynamic balloon mounted on the distal end section of the sleeve tube. In some embodiments, the diameter of the balloon may be adjusted by increasing the volume of air or gas forced into the balloon. In some embodiment, inflation of the balloon may cause the working section of the tube sleeved to curve or further curve.

In some embodiments, the sleeve tube of the present disclosure can include a soft, tapered distal nose or tip that can, in some applications, facilitate smoother and less traumatic insertion of the sleeve tube into the patient's mouth, esophagus, and stomach, reducing the incidence of sore throat, tearing of the esophageal lining, and esophageal bleeding.

In some embodiments having a curved or curvable working section, one or more portions of curvature can established using a plurality of thermoplastic materials having "shape memory" properties that cause the working section to be biased toward providing a predetermined curvature at certain temperatures, such as the internal temperature of the lumen of the stomach, and to be biased toward be straight in the free state at normal room temperature.

In some applications, when the sleeve tube is inserted into the stomach, the temperature of the stomach causes the working section to curve to conform more closely to the natural curvature of the interior stomach wall.

Other embodiments may provide a sleeve tube with a flexible, resilient working section permanently biased to a predetermined curved free state. In some applications, the working section can easily straighten for insertion or withdrawal through the patient's esophagus while returning to the curved state in the patient's stomach.

In another aspect, the predetermined curved free-state working section can conform to human anatomy in two respects and can therefore improve safety of insertion and improved positioning of the working section.

First, the predetermined curvature can, in at least one portion of the working section such as the distal tip for example, approximate the curvature of human anatomy upon the transition from the esophagus into the stomach and thus facilitate insertion across the esophagus-to-stomach threshold more safely and smoothly.

Second, the predetermined curvature can also, in at least the one or another portion of the working section that may or may not include the tip, approximate the curvature of a portion of the natural human stomach, such as adjacent the incisura, and thus allow placement of the tube within the stomach with more accurate surgery and less distortion of natural shape of the human stomach.

Other advantages of various embodiments of the sleeve tube can variously include the reduction in complications such as leaks, stenosis, obstruction, and/or encroachment at the incisura which results in improved patient outcomes, decreased complications, and reduction in costs that would otherwise be incurred during the corrective procedures and subsequent medical care.

At least some embodiments of a curved working end on a sleeve tube can prevent, or at least reduce the likelihood of, the "wind sock deformity," by maintaining an anatomic curve of the stomach.

At least some embodiments provide a working end having greater volume and/or width to provide a surgical calibration guide. Some applications can use the calibration guide to determine (i) where to staple or otherwise close off a section of a stomach and/or (ii) how much of the stomach to remove. The calibration guide can therefore prevent, or at least reduce the likelihood of, an unduly narrow residual stomach sleeve.

Some applications provide length calibration markings along the outer periphery of the sleeve tube. These calibration markings can be used to identify how much of the sleeve tube has been inserted into a patient.

This disclosure also provides a novel system and method of fabrication and use of a multi-channeled sleeve tube.

There are many other novel features and aspects of this disclosure. The will become apparent as this specification proceeds. It is to be understood, however, that the scope of a claim in this matter is to be determined by the claim as issued and not by whether the claim addresses an issue, or provides a feature, because the issue or feature is referenced in the Background or Brief Summary sections above.

BRIEF DESCRIPTION OF THE DRAWINGS

The applicants' preferred and other embodiments are described in association with the accompanying Figures in which:

FIG. 4A is a partial cross-sectional view taken along section line A-A of FIG. 1, showing an inflatable balloon component in an inflated state;

FIG. 4B is a partial cross-sectional view of the structure of FIG. 4A with the balloon in the deflated state;

FIG. 5 is a cross-sectional view taken along section line D-D of FIG. 1, showing a section of a coupler and multiple channels of the sleeve tube of FIG. 1;

FIG. 6A is a cross-sectional view of an alternative structure for the multiple channels in a sleeve tube;

FIG. 6B is a cross-sectional view of a yet further structure providing multiple channels in a sleeve tube;

FIG. 7A is a cross-sectional view taken along section line B-B of FIG. 1, showing the balloon in an inflated state;

FIG. 7B is a cross-sectional view of the structure of FIG. 7A with the balloon in a partially deflated state

FIG. 13 is a partial side elevational view of the sleeve tube of FIG. 10 with the balloon inflated;

FIG. 14 is cross-sectional view taken along section line F-F of FIG. 10;

FIG. 15 is a cross-sectional view taken along section line G-G of FIG. 10;

FIG. 16A is a cross-sectional view taken along section line H-H of FIG. 10, showing the balloon in the inflated state;

FIG. 16B is a cross-sectional view of the structure of FIG. 16A but with the balloon deflated;

DETAILED DESCRIPTION OF SOME EMBODIMENTS

The prior Brief Summary and the following description provide examples that are not limiting of the scope of this specification. One skilled in the art would recognize that changes can be made in the function and arrangement of elements discussed without departing from the spirit and scope of the disclosure. Various embodiments can omit, substitute, add, or mix and match various procedures or components as desired. For instance, the methods disclosed can be performed in an order different from that described, and various steps can be added, omitted, or combined. Also, features disclosed with respect to certain embodiments can be combined in or with other embodiments as well as features of other embodiments.

Figure 1:
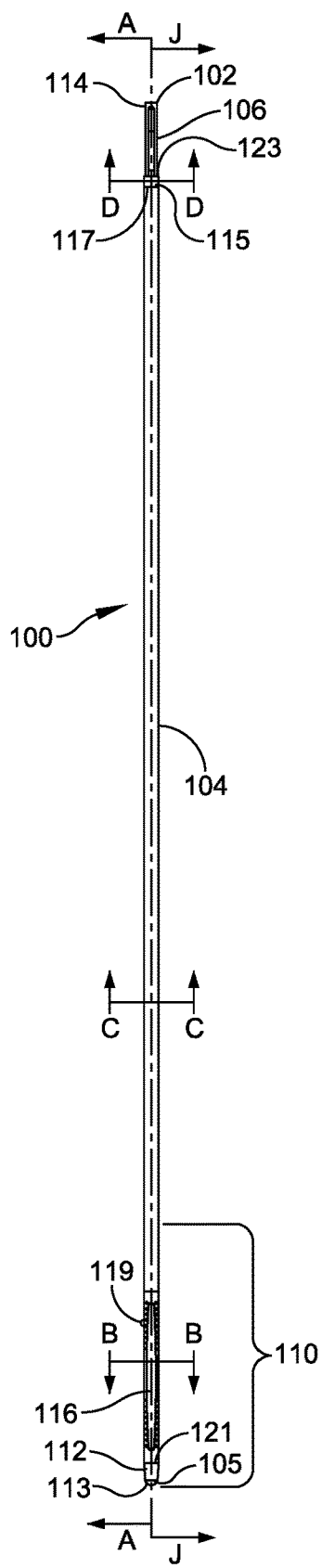
FIG. 1 is an elevational view of an embodiment of three-channel sleeve tube.

Referring now to FIG. 1, one embodiment an elongated sleeve tube 100 has a proximal end 102 opposite a distal end 105. The sleeve tube 100 can provide a multi-channel orogastric tube system for use in conducting sleeve gastrectomy surgery. In other embodiments, the sleeve tube 100 also or alternatively can be used as a calibration device within the lumen of a person's stomach.

The sleeve tube 100 may be conceptually divided into four sections: the elongated sleeve tube 100 as a whole; an aperture section 106 providing differing apertures for each of the three tubular channels or conduits; a main body section 104 secured to the distal end of the aperture section 106 and having three tubular channels extending longitudinally within and along the length of the sleeve tube 100; and an expandable section 110 extending from the main body section 204 at the distal end 105 of the sleeve tube 100. The expandable section 110 terminates in a tapered nose section 112 at the distal end 113 of the expandable section 110.

Aperture section 106 attaches to the main body section 204 by way of a tubular coupler end section 115 at the distal end 123 of the aperture section 106. In turn, the main body section 104 penetrates the distal end 117 of the coupler end section or sleeve 115 to couple the main body section 104 to the aperture section 106.

In some embodiments, a balloon 116 is mounted to, or formed in, the expandable section 110 of the sleeve tube 100. The balloon 116 can be controllably inflated outwardly from, and controllably deflated to retract toward, the body 119 of the expandable section 110.

The sleeve tube 100 can thus be formed of separate sections and elements, for example, 106, 104, 110, and 112, joined together by adhesives or other inter-connecting devices or methods (for example, by thermal bonding or fusing techniques). The adhesives can be, but are not limited to, Federal Drug Administration (FDA) approved medical adhesive materials (for example, Luer-Lok, Luer-Slip, catheter tip, barbed fittings, solvents, etc.). In other embodiments, the sleeve tube 100 may be molded (for example, by extrusion or injection molding) as a single piece without the need to join together multiple pieces. In yet other embodiments, the sleeve tube 100 or any of its components can be three-dimensionally printed using polymeric or other suitable material.

In one embodiment, the nose section 112 is first formed as a separate unit from the balance of the expandable section 110 and secured to the balance of the expandable section 110 with medical adhesive or other coupling devices or methods as described above. The nose section 112 is frustoconical, or somewhat so, to provide a conically narrowing but rounded distal end 113 of the nose section 112 opposite its junction with the balance of the expandable section 110. The proximal end 121 of the nose section 112 secured to the balance of the expandable section 110 is approximately the same diameter in width as the balance of the expandable section 110 (e.g., 13.3 mm or 40 Fr).

In some embodiments, the nose section 112 is made of the same material as the balance of the expandable section 110 (and may formed as part of it) to provide similar flexibility and resilience for the expandable section 110 and the nose section 112. In some embodiments, the nose section 112 provides an atraumatic distal end 105 that can help prevent mucosal trauma as the sleeve tube 100 is inserted into the patient's body.

Figure 2:
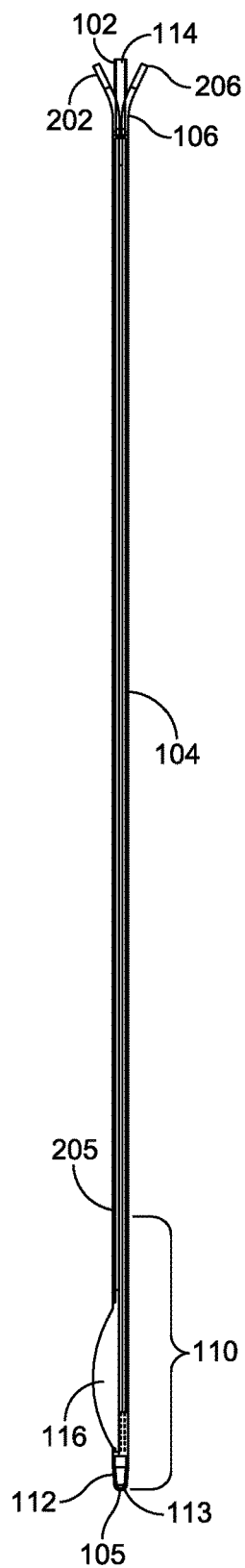
FIG. 2 is a partial cross-sectional view taken along section line A-A of FIG. 1.

With reference now to FIG. 2, the aperture section 106 has three separate channels or tubes 114, 202, 206 providing three corresponding tubular lumens (that is, cavities or passages), with these lumens extending from the aperture section 106 longitudinally through main body section 104 to penetrate the expandable section 110 of the sleeve tube 100. The expandable section 110 extends from the distal end 205 of the main body section 104 and includes an outwardly inflatable balloon 116, shown in an inflated state in FIG. 2.

Figure 3A:
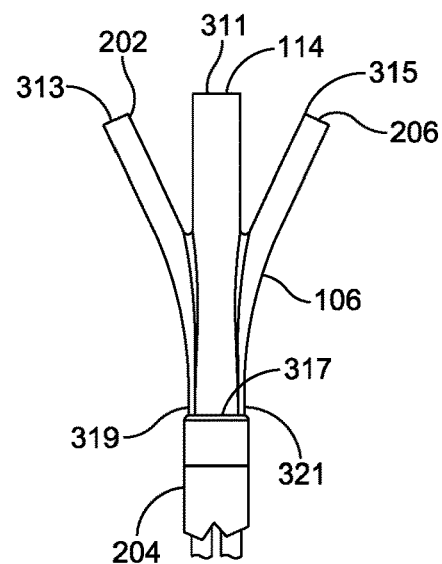
FIG. 3A is an elevational view of an aperture section mounted to the main body section of the sleeve tube of FIG. 1.

With reference now to FIG. 3A, the tubular proximal ends 311, 313, 315 of the main channel 114, balloon channel 202, and sump channel 206, respectively can inter-connect with syringes, suction devices, or stopcocks as desired. The opposed ends 317, 319, 321 of the main channel 114, the balloon channel 202, and the sump channel 206, respectively, converge to penetrate the main body section 104 and provide a multi-channeled tubular main body section 204 having a tubular outer periphery surrounding the main channel 114, balloon channel 202, and sump channel 206 contained within the tubular outer periphery of main body section 104.

Figure 3B:
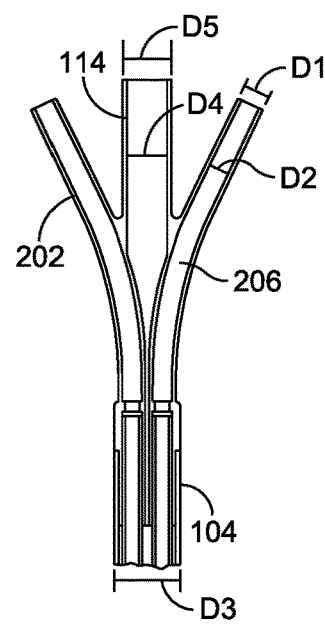
FIG. 3B is a cross-sectional view of the structure of FIG. 3A.

With reference to FIG. 3B, the outer diameter D1 of the balloon channel 202 is the same as the outer diameter of the sump channel 206, whereas the outer diameters D3 and D5 of the main channel 114 and main body section 104, respectively, are larger than D1. In yet other embodiments, the outer diameters of channels 202, 204, and 206 may otherwise differ or be the same as desired, and thus they may all differ from one another, respectively, if desired for a given application.

Similarly, the inner diameters (that is, the lumen diameters) of the balloon channel 202 and sump channel 206 may have the same, or approximately the same, diameter D2, including extending along and within the lateral length of the main body section 104. The inner diameter D4 of the main channel 114 may be larger than D2. In yet other embodiments, the inner diameters of channels 202, 204, and 206 may all differ from other another, respectively, or be similar as otherwise desired.

In one example, D3 may be between 28 Fr and 52 Fr, with a preferred diameter of 40 Fr. These exemplary diameters may be altered as desired.

With reference to FIGS. 4A and 4B, the expandable section 110 has a central laterally extending, generally tubular section 401 extending from the main body section 104 and terminating in the nose section 112. The balloon 116 is securely mounted in a balloon mounting slot 403 penetrating, and laterally extending along, the outer periphery 405 of the central generally tubular section 401, The distal end 407 of the main tube section 204 has a thinned wall 409 providing a female distal receptacle 409 to matingly surround, abut, and grasp (in conjunction with adhesive to form a secure bond with) a narrowed mating male proximal end 411 of the expandable section 110. The distal end 413 of the balloon tube 202 connects to the proximal end 415 of the balloon 116 so that the balloon tube 202 can thereby (i) inject air or other gas into the balloon 116, causing the balloon 116 (i) controllably inflate by injecting air or other gas in the proximal end (not shown in FIGS. 4A and 4B) of the balloon channel 202, and (ii) controllably deflate by venting or withdrawing air or other gas from the proximal end (id.) of the balloon channel 202 to, with reference to FIG. 4B, collapse the balloon 116 within the balloon mounting slot 403. In the deflated state, the outer periphery of the balloon 116 lies flush with the outside surface of the curved working section 110. In this deflated state, the sleeve tube 100 may be inserted through the patient's mouth and esophagus and into the patient's stomach.

With continuing reference to FIG. 4B, the sump channel 206 extends past the female distal receptacle 409 well into the general tubular interior of the generally tubular section 401. The generally tubular section 401 has multiple laterally extending rows, e.g., 417, 419, of tubular perforations, e.g., 421, 423, penetrating the generally tubular section 401 and extending from the interior to the outer periphery 405 of the generally tubular section 401. The sump channel 206 thus can be used to withdraw or inject gas into the generally tubular section 401, and the main channel 114, which is in communication with the interior of the generally tubular section 401, can inject or withdraw gas, and withdraw material from, the interior of the generally tubular section 401 through the perforations, e.g., 421, 423, in that section 401. Material or gas sucked into the generally tubular section 401 can be withdraw from the stomach through the main channel 114, and the sump channel 206 can be used to inject air or gas into the generally tubular section 401 in order to, for example, clear blockage of material within the perforations, e.g., 421, 423. The sump channel 206 can alternatively be used to aspirate gastric contents of the patient's stomach.

In contrast, a single channel tube system (for example, in procedures using multiple separate tubes) may clog easily, thus resulting in a failure to successfully evacuate gastric contents. The sump channel 206, as part of the multi-channel system 100, allows air to travel through the system and provides a secondary channel that may be used to clear a clogged tube, thus improving the effectiveness when the system is used as an evacuation tool for gastric contents. Furthermore, use of the sump channel 206 can be used to vent the main channel 114 reduce the risk of applying too much suction pressure to the main channel 114, resulting in gastric mucosal lining tissue being pulled toward and within perforations, e.g., 421, 423, in the sleeve tube 100, which can lead to tearing of the stomach lining or bleeding when the sleeve tube is removed.

The balloon 116 may be fabricated by dip forming of a thermoset polymer, or by blow molding or extrusion of a thermopolymer, such as polyvinyl chloride, polyurethane, etc. The balloon 116 may be affixed to the balloon mounting slot 403 with compatible medical adhesives, by heat shrinkable tubing, by mechanical means such as thread ties for example, or by a combination of such techniques and/or others.

In one embodiment, the uninflated width W1 of the inflatable section 110 is 10 mm and the lateral length of the balloon 116 is 6 cm, with the distal end 427 of the balloon 116 spaced 2 cm from the distal end 105 of the sleeve tube. When air or other gases are inserted into the balloon 116, the balloon inflates to cause the width of inflatable section to increase to, for example, 23.3 mm. The volume of the balloon can 116 vary of course, and in some embodiments, the balloon can fully inflate when pressurized with air or gas to 2 ATM. In addition, the balloon may be further pressurized to provide a more rigid balloon for greater support.

With reference now to FIG. 5, the balloon channel 202 and the sump channel 206 may be located inside and coupled to, or abutting, the interior side wall of the main body section 104. Alternatively, as shown in FIG. 6A, the balloon channel 202 and the sump channel 206 may be spaced from the interior side or wall of the main channel 204.

In another alternative of FIG. 6B, the main body section 204 includes an interior tube 602 extending inwardly from the interior surface 604 of the main tube 602. The portions of the balloon channel 202 and sump channel 206 within the main body section 104 can consist of separated, opposed D-shaped channels sharing a common central wall 605 within the interior tube 602. A laterally extending portion of the interior tube 602 penetrates, and is partially formed within, a portion of the wall of the main body section 104.

With reference now to FIGS. 7A and 7B, a static, secured portion 704 of the balloon 116 is secured to the interior wall of the portion balloon channel 202 within the balloon mounting slot 403 in the expandable section 110. As it is inflated, the balloon 116 extends outwardly from balloon mounting slot, and in the embodiment of FIG. 7A, the balloon 116 expands to provide an inflated section 702 having an oblong cross-section extending from, and along the lateral length of, the U-shaped balloon mounting slot 403.

Figures 8A, 8B:
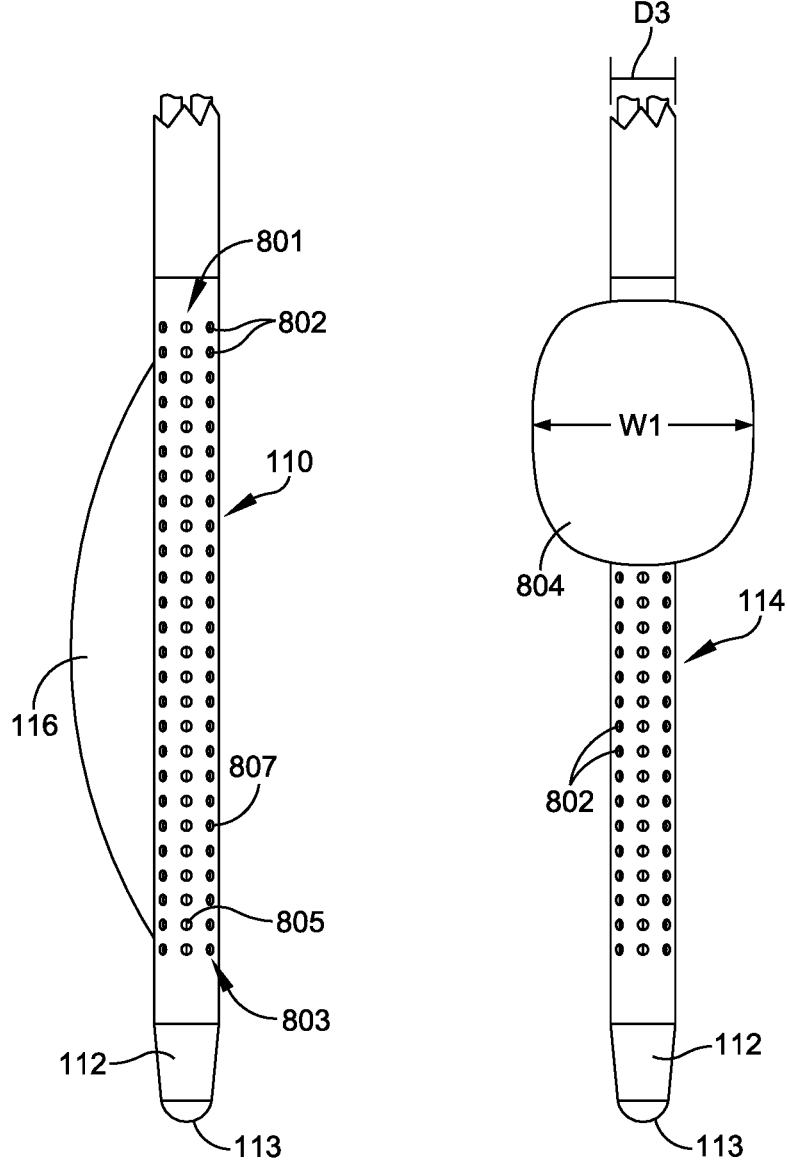
FIG. 8A is a partial elevational view of a section of the sleeve tube of FIG. 1 adjacent the sleeve tube's distal end.
FIG. 8B is a partial elevational view showing an alternative balloon shape provided adjacent an alternative sleeve tube's distal end.

With reference to FIG. 8A, the parallel rows of perforations, e.g., 801, 803, extend laterally along, and all around the general tubular periphery of the bulk of the expandable section 11. In one embodiment, the rows of perforations, e.g., 801, 803, are located within 15-20 cm of, as shown in FIG. 1, the distal end 105 of the sleeve tube 100. The number, size, and location of the perforations, e.g., 805, 807, can be varied to facilitate removal of particulates when suction is applied to the main channel 204 (not shown in FIG. 8A). In addition, the perforations, e.g., 805, 807, can enable a leak test in which colored dye is forced into the sleeve tube 100 to fill the stomach through the perforations, e.g., 805, 807, to distend the stomach and test a surgical staple line for leakage Referring now to FIG. 8B, an alternative embodiment of the expandable section 110 has a differing or additional balloon 804. This balloon 804 expands to provide a rounded exterior periphery substantially wider W3 than external diameter D3 of the balance of the laterally extending expandable section 110.

In another embodiment (not shown), yet another balloon structure, along with a supporting channel, can be also be included in a single sleeve tube to augment the diameter of the sleeve tube at, for example, just below the mid-stomach, in the region of the incisura. This location is an area where surgeons generally should avoid encroachment and making the stomach too tight, which can result in leaks and strictures.

Figure 9:
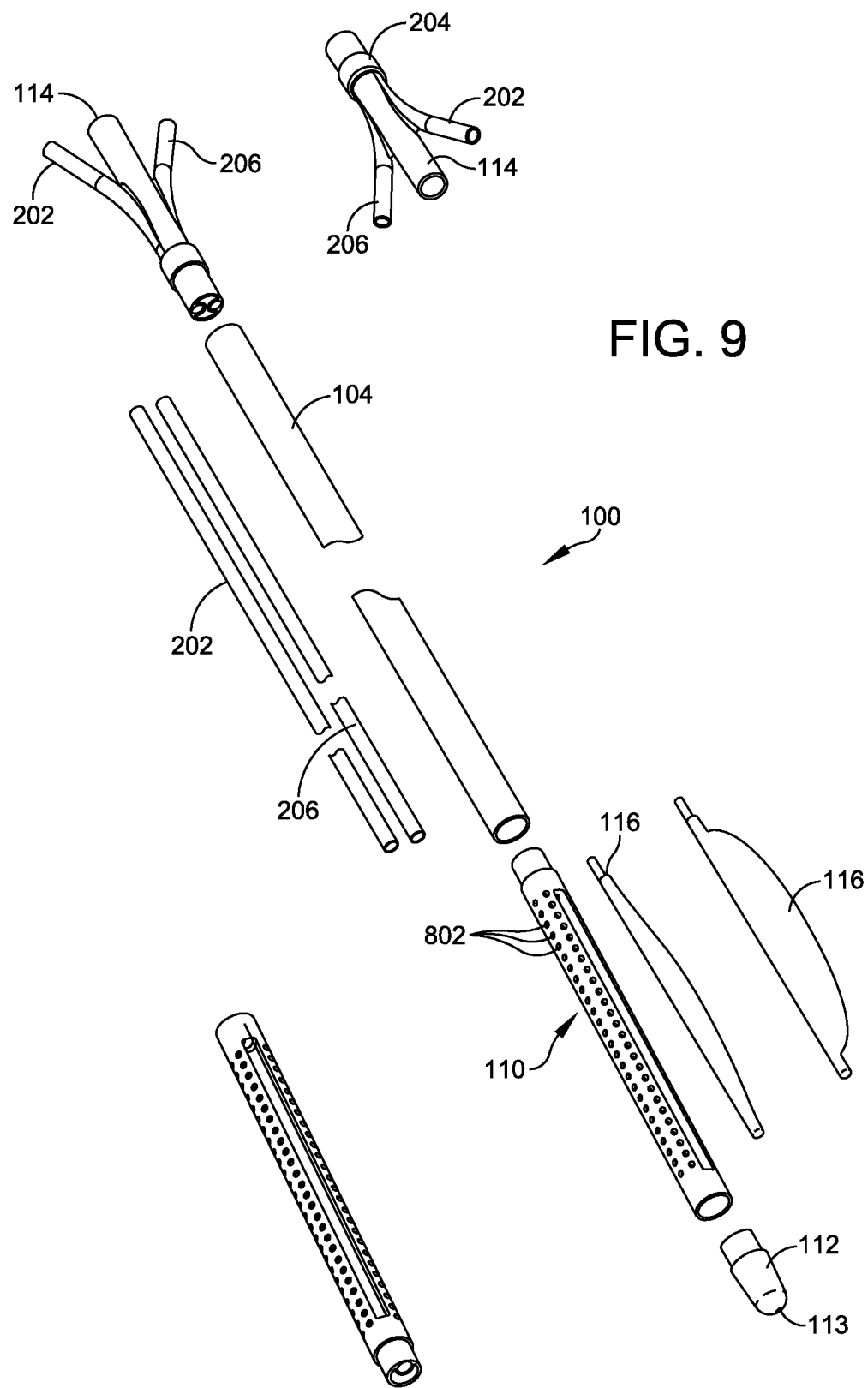
FIG. 9 shows an exploded perspective view of the sleeve tube of FIG. 1.

With reference now to FIG. 9, the sleeve tube 100, including any or all of the associated sections and parts, may be manufactured in any of many ways. In one example, each of the elements of sleeve tube 100 shown in FIG. 9 may be fabricated individually and then subsequently assembled into the completed sleeve tube 100. In some embodiments, the sleeve tube 100 may be molded in two halves (less the balloon) combined to form a complete device from a thermoset material (silicone for example). The balloon can then secured to the sleeve tube 100 with adhesive.

In another example, at least the main body section 104 may be injection molded using a thermoset material (silicon for example), with each of three channels 202, 204, and 206 created by inserting long core pins that are removed after the entire sleeve tube assembly is removed from the mold.

In yet another example, elements of the sleeve tube 100 assembly such as shown in FIG. 9 may be extruded or molded separately of silicone rubber. More specifically, the sleeve tube's main body section 204 can be formed of extruded silicone rubber formed with a distal end curvature before vulcanizing. The branching aperture end 106 can be injection molded. The expandable section 110 can be injection molded to provide the perforations 802 and balloon mounting slot 403 (or other balloon mounting structure), and nose section 112. After production, the parts can be bonded together such as with adhesive or other bonding techniques well known in the art. Other methods of production may be utilized, such as three-dimensional printing for example.

In order to facilitate passage of the sleeve tube 100 into the stomach and to enable the creation of the adjustable curvature of the curvable working section 110, the sleeve tube 100 can be fabricated or coated with a low friction polymer, such as, but not limited to, polytetrafluoroethylene (PTFE) or other hydrophilic materials. In one embodiment, at least the working section 110 alternatively at least dominantly consists of silicone, with curvature of this section 100 formed a in a secondary curing process.

In some embodiments, each or any of the parts, sections, or elements described may be symmetrical along an axis; however, in other embodiments, the parts, sections, or elements may be asymmetrical. For example, a proximal end may be thicker than a distal end, or different materials may be used at one end versus another. In some cases, the material may be patterned in one section and not in others.

In one embodiment, the sleeve tube 100 is approximately 100 cm in length from the proximal ends of the tube at the aperture section 106 to the distal end 105 of the nose section 112 and has a diameter of approximately 13.3 mm (40 Fr). These dimensions may be adjusted as needed or desired for differing applications. Generally, however, the diameter of the sleeve tube 100 for human gastric applications may be up to 150% greater than 13.3 mm, and the length of such a sleeve tube may be up to 75% shorter and 100% longer than 100 cm.

When the sleeve tube 100 is properly placed within a patient's stomach, the balloon 116 may be inflated at a desired location within the stomach, such as at the gastric incisura or other desired locations causing them to similarly inflate. The ability to increase the diameter of the sleeve tube (and more specifically the curvable working section 110 of the sleeve tube 100) may result in improving the safety of the sleeve procedure and/or prevent complications resulting from stenosis, staple link leaks, or gastric obstruction.

A primary risk factor in the development of gastric staple line leaks is the development of narrowing or stenosis at the lower part of the sleeve, which then increases the intraluminal pressure, causing leaks. Some embodiments prevent this occurrence through the inflation of balloon 116, which can add an additional up to 5-25 mm of width, and in one particular embodiment up to 10 mm of width, to the sleeve tube 100 at locations where stenoses typically form (for example, in the lower sleeve incisura region). After the sleeve procedure is completed, and the leak test is finished, the balloon 116 is deflated, and the sleeve tube 100 is removed from the patient.

In some embodiments, the sleeve tube 100 may be used for veterinarian applications. The lengths, diameters, and thicknesses, etc., of the sleeve tube 100 and corresponding components may be sized appropriately for such applications.

Figures 10, 11, 12A, 12B:
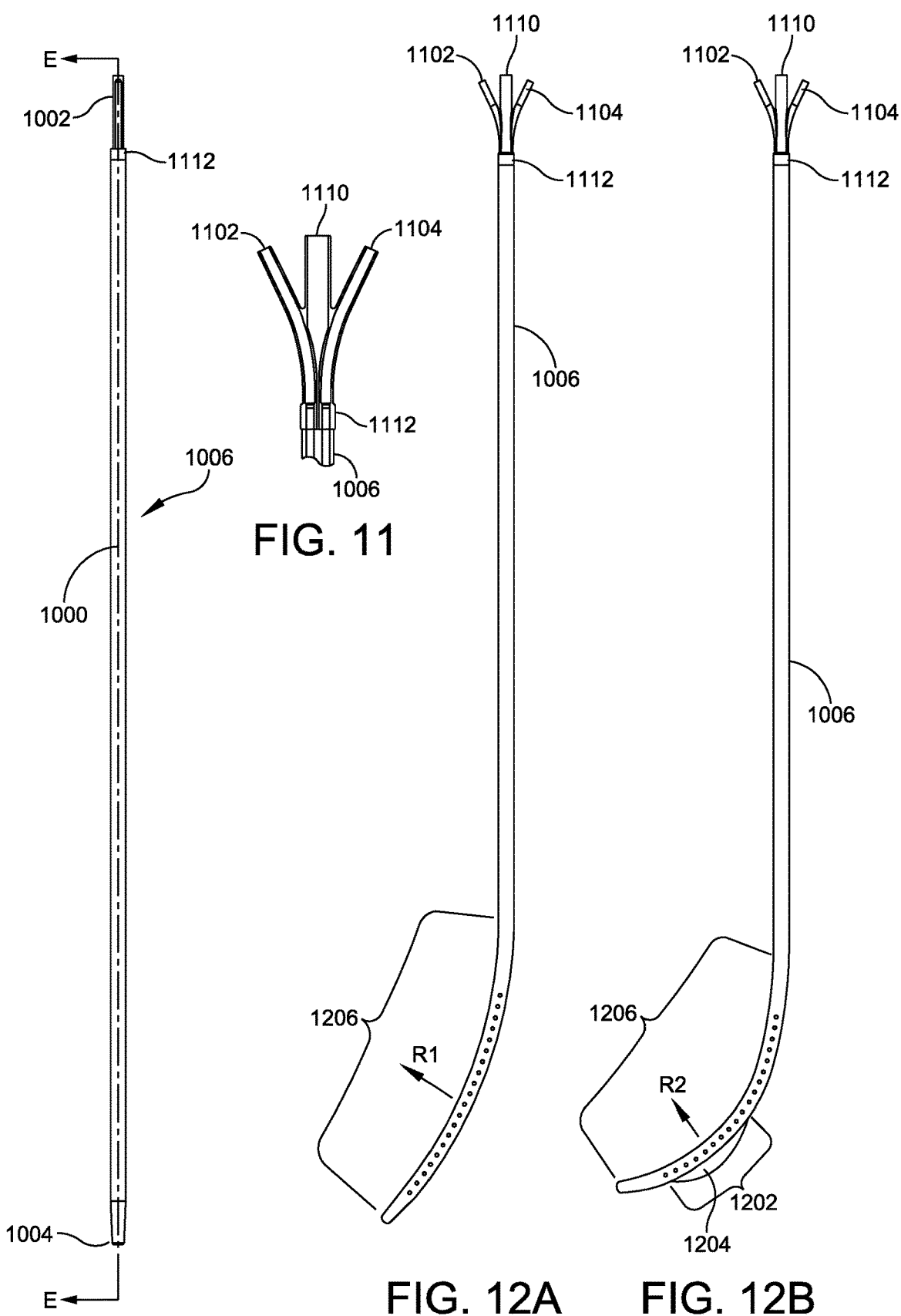
FIG. 10 is a front elevational view of an alternative three channel embodiment of a sleeve tube.
FIG. 11 is a partial cross-sectional view, taken along section line E-E of FIG. 10, of the aperture section secured to the main body section.
FIG. 12A is a side elevational view of the sleeve tube of FIG. 10.
FIG. 12B is a side elevational view of the sleeve tube structure of FIG. 12A with the balloon inflated to cause further curvature of the working end of the sleeve tube.

Turning now to FIG. 10, an alternative sleeve tube 1000 has an integral silicone main body 1006 with a proximal end 1002 opposite a distal end 1004. With reference to FIG. 11 a main channel 1110 and opposed balloon 1102 and sump 1104 channels feed together through a sealing sleeve 1112 into the main body section 1006. Conversely, the opposed balloon 1102 and sump 1104 channels extend upwardly from the sealing sleeve 1112 and bend away spaced from each other 1102, 1104, providing a spread and forked configuration of the ends of main channel 1110, balloon channel 1102, and sump channel 1104 opposite the sealing sleeve 1112. The width of this spread and forked configuration can make it impossible for the proximal end 1002 of the sleeve tube 1000 to penetrate the patient's mouth.

Referring to FIG. 12A, the sleeve tube 1000 assembly is formed to have a predetermined curved shape by placing the sleeve assembly 1000 in a curing cavity (not shown) having a predetermined curved section causing the curvable working section 1206 to curve within the cavity at a radius R1. Heat or another curing agent is then applied, causing the working section 1206 to bias toward taking on the predetermined shape of radius R1 when working section 1206 is subject to certain temperatures, such as when in the stomach of a patient. Depending on the materials used and the temperature of the working environment, the curvable working section 1206 can resume a straightened form when the sleeve tube 1000 is removed from the cavity and cools to room temperature, and then similarly return to having the pre-determined curvature when the curvable working section 1206 reaches the pre-determined temperature inside a patient's stomach.

With reference to FIG. 12B, when the sleeve tube and balloon 1000 is then inserted in a patient's stomach and the balloon 1204 is inflated by injecting gas into balloon channel 1102, the inflating balloon 1204 forces the adjacent portion 1202 of the curvable working section 1206 to curve more that the predetermined curvature provided by heating of the working section 1206 within the stomach. As result, the inflated balloon 1204 forces the adjacent portion 1202 of the working section 1206 to have a radius R2 smaller than, as shown in FIG. 12A, radius R1.

In one embodiment, the sleeve tube 1000 is made from silicone having a Shore hardness on the A scale of 25 to 30. The silicone can be, for example, SILASTIC® brand biomedical grade Liquid Silicone Rubber (LSR) from Dow Corning or Thermoset Elastomer (TSE), such as Dow Corning SILASTIC® 7-4860 BIO LSR (heat cured) or Dow Corning SILASTIC® Q7-4535 BIO ETR Elastomer (peroxide cured)). In some embodiments, the silicone or other material should be of medical grade, have maximum lubricious characteristics, and be directly bondable.

FIG. 13 is a partial elevational view of the sleeve tube 1000 of FIG. 10 with the working section 1206 in a curved configuration. With reference to FIG. 14, the opposed balloon channel 1102 and sump channel 1104 abut opposed interior sides of the interior wall of the main body section 1006. The remaining space 1404 within the of the interior of main body section 1006 provides a main body section channel 1404 in communication with, as shown in FIG. 13, the upwardly extending main channel 1110. In other words, with reference back to FIG. 14, the main body section 1006 has three interior, axially extending lumens 1402, 1404, and 1406 in communication with, as shown in FIG. 14, the balloon channel 1102, the main channel 1110, and the sump channel 1104, respectively. The balloon channel 1102 and sump channel 1104 abut the opposed sides of the internal periphery of the main channel 1110 so that the exterior periphery of the main body section 1006 may be tubular and thus enable easier insertion and bending of the sleeve tube 1000 during insertion into the body.

With reference now to FIG. 15, the working section 1206 in sleeve tube 1000 has laterally extending rows (not shown in FIG. 15) of tubular, radially extending perforations or passages 1501, 1503 passing from the exterior periphery of the working section 1206 into the main body section channel 1404. Gas and material can pass through these radial passages 1501, 1503.

With reference now to FIGS. 16A and 16B, the lower end of the working section 1206 provides a laterally extending balloon channel 1601 having a relatively thin outer wall 1603 as compared to the inner wall 1605 of the balloon channel 1102. The opposed portions of the main channel 1006 are also thinned at this location. Then, as shown in FIG. 16B, the relatively thin walled section 1603 provides the exterior wall of the balloon 1605 in its collapsed state. The thin walled section 1603 balloon can then, as shown in FIG. 16A, be blown up as shown in FIG. 16A and then subsequently, as shown in FIG. 16B, again be deflated to its collapsed state.

Figure 17A:
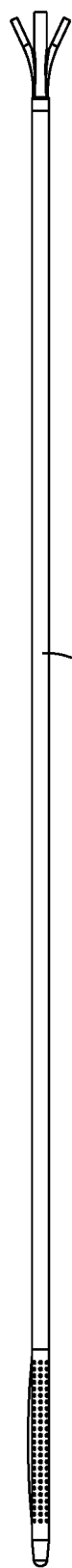
FIG. 17A is an elevational view of the sleeve tube of FIG. 10 in a pre-curved or otherwise straightened state.
Figure 17B:
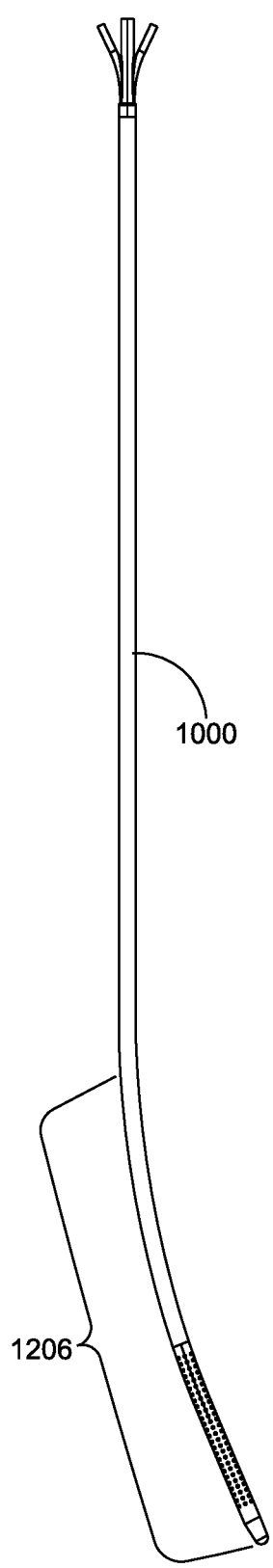
FIG. 17B is an elevational view of the sleeve tube of FIG. 17A in a partially curved state.
Figure 17C:
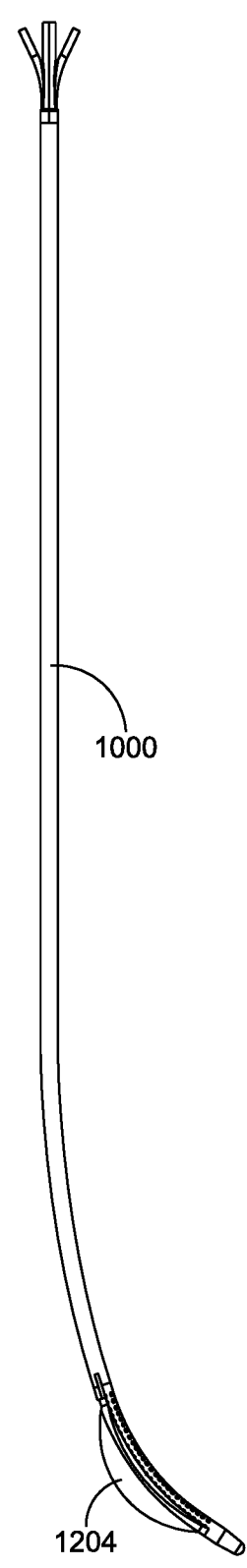
FIG. 17C is an elevational view of the sleeve tube of FIG. 17B in a further curved state brought about by inflation of a balloon in the curved section.

With reference to FIGS. 17A, 17B, and 17C, the sleeve tube 1000 may be fabricated as a single part multilayer co-extrusion. With reference to FIG. 17A, a blank of the entire sleeve tube 1000 may be extruded from multiple thermoplastic elastomers with different glass transition temperatures. Then, with reference to FIG. 17B, the entre blank can then be heated to glass transition temperature, with the working section 1206 thermoformed to create the curvature and perforations as shown in FIG. 17B. Subsequently, the now-thermoformed sleeve tube can be heated to the glass transition temperature for the balloon channel 202 in order to secure the balloon 116 to the balloon channel slot or wall 403 (not shown in FIG. 17B). The entire device may be sealed in ways well known in the art.

In use, the working section 1206 is straightened and inserted into the patient's mouth, esophagus, and stomach. Within the stomach, the working section 1206 returns to its free, curved state as in FIG. 17B. Then, with reference to FIG. 17C, the balloon 1605 may be inflated by the practitioner to cause the working section 1206 abutting the balloon 1605 to further curve within patient's stomach. Conversely, the balloon 1605 may be deflated to cause the working section 1206 to return to its free state and allow the sleeve tube 1000 to be withdrawn from the patient. During withdrawal, the flexible working section 1206 flexibly straightens, as in FIG. 1, to pass through the esophagus without causing edema to the patient.

In an exemplary gastrectomy procedure, the sleeve tube includes a balloon channel, a main channel, and a sump channel, all extending from the proximal end of the sleeve tube to the working, distal section of the sleeve tube. The distal end of the sleeve tube is inserted into a patient's and through the patient's esophagus into the patient's stomach. Laparoscopic technology can also be utilized to operation personnel to view the placement of the sleeve tube on video monitors present in the operating room.

In some cases, the sleeve tube may be comprised of a low friction material to facilitate easier entry into the body. The sleeve tube may alternatively or in addition be lubricated with a water-soluble lubricant prior to the insertion step.

First, gastric contents are aspirated from within the lumen of the stomach through perforations in the working end of the sleeve tube and then through the main channel and possibly the sump channel as well.

The sleeve tube is then advanced into the stomach so that its distal tip passes along the lesser curvature aspect of the stomach. Operation personnel can adjust the working section of the sleeve tube to provide the proper placement, adjustment of the sleeve tube curvature, and inflation of the sleeve tube balloon as desired.

When the sleeve tube is in position, the desired curvature is established by inflating a balloon in the distal end section of the sleeve tube. Calibration markings of the tube can be read at the lips of the patient, assessing the number of centimeters (or other unit of measurement) the tube has been advanced into the patient. When the sleeve tube is in position, it is noted to be conforming to the natural curvature of the human stomach. The thickened curved distal end section of the tube is brought to the position of the incisura of the human stomach. The operation personnel can then use conventional suction techniques to apply suction to the main suction tube to hold gastric tissues snugly to the tube so that the surgery may then proceed. As a result, the sleeve tube can also serve as a stomach sizing device, enabling the surgeon to remove the outer portion of the stomach safely and staple the residual stomach sleeve shut.

After completion of the sleeve tube gastrectomy procedure, the surgeon can also use the sleeve tube to perform a leak test to test the integrity of the staple line on the stomach. A leak test can be done by injecting colored dye into the main channel of the multi-channeled sleeve tube while the surgeon occludes the sump outlet, thus tautly distending the stomach and stressing a newly created staple line. The surgeon can then observe the integrity of the staple line. When desired, the dye is aspirated through the main channel, the balloon is deflated, and the sleeve tube is then removed from the patient.

The sump channel can be used during the procedure to inject gas or air into the distal end section of the sleeve tube. The sump channel can thus aid to clear blockage of sleeve tube perforations and the main channel. The sump channel can also be used to prevent excessive sucking through the main channel and the associated perforations in communication with the main channel.

Figure 18:
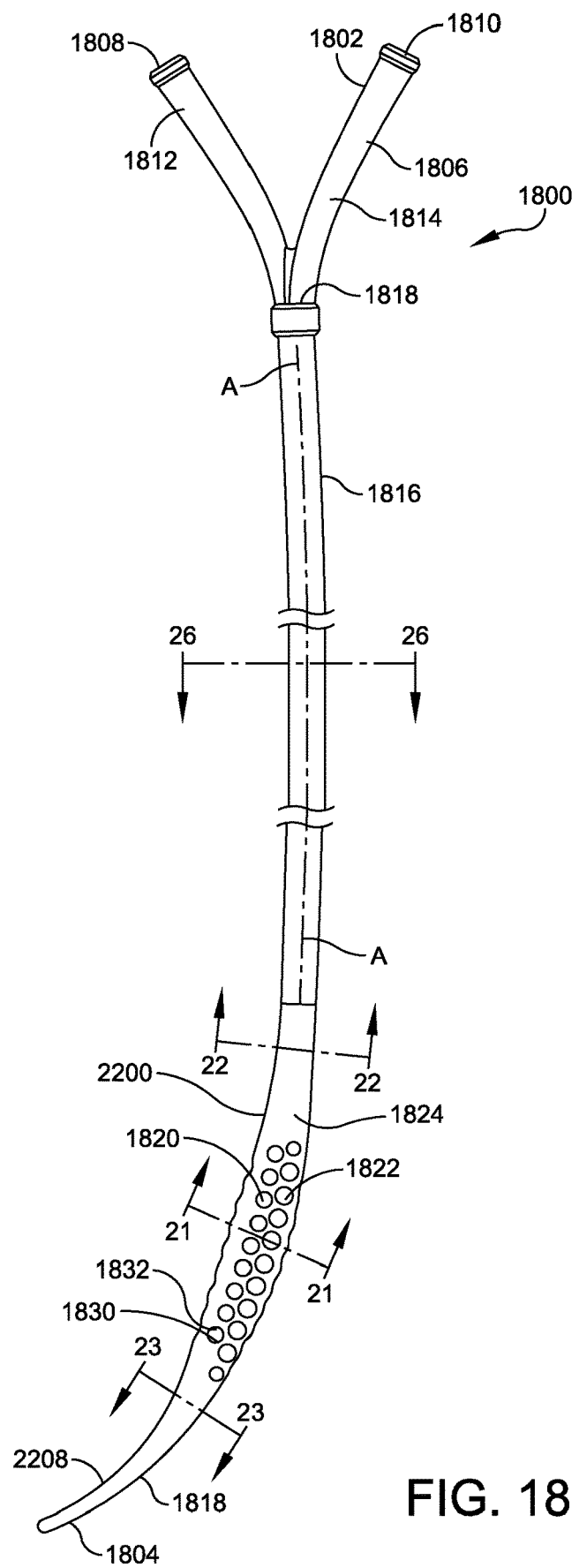
FIG. 18 is a partial front elevational view of a two-channel example embodiment of a sleeve tube.

With reference now to FIG. 18, a third sleeve tube embodiment, generally 1800, also has a proximal end 1802 opposite a distal end 1804. This sleeve tube 1800 also can provide a multi-channel orogastric tube system for use in conducting sleeve gastrectomy surgery. Similarly, in other embodiments this sleeve tube 1800 can be used as a calibration device within the lumen of a person's stomach.

The sleeve tube 1800 conceptually includes four sections: an elongated sleeve tube as a whole 1800, a proximal aperture section 1806 providing proximal sump and suction apertures 1808, 1810 for sump and suction tubular conduits 1812, 1814, respectively, a main body section 1816 secured to the distal end 1818 of the aperture section 1806 and having two internal tubular channels or lumens (not shown in FIG. 18) extending longitudinally within, and along the length of, the main body section 1816, and a distal section 1818 in communication with the two tubular channels (not shown) within the main body section 1816. As explained in detail infra, some third sleeve tube embodiments can provide a distal end 1818 having a curvature generally resembling a common interior curvature of human stomachs, though other curvatures may be provided as desired.

The distal section 1818 has a curved first row of 9 cavities 1820 providing flexion reliefs 1820 to allow the distal section 1818 to more easily bend at the location of the flexion reliefs by collapsing the laterally opposed sides, e.g., 1830, 1832, of the flexion reliefs towards each other. The distal section 1818 also has a curved first row of distal suction apertures 1822 in material transfer communication with the proximal suction aperture 1810 through the intermediate body section 1816 and suction conduit 1814. The curved first row of flexion reliefs 1820 is adjacent the first row of distal suction apertures 1822 extending laterally along the lateral length of the distal section 1818. The first rows of flexion and suction apertures 1820, 1822, respectively, also each penetrate the periphery 1824 of the distal section 1818 transverse to the plane of curvature of the distal section 1818 away from the axis A-A of the main body section 1816

Figure 19:
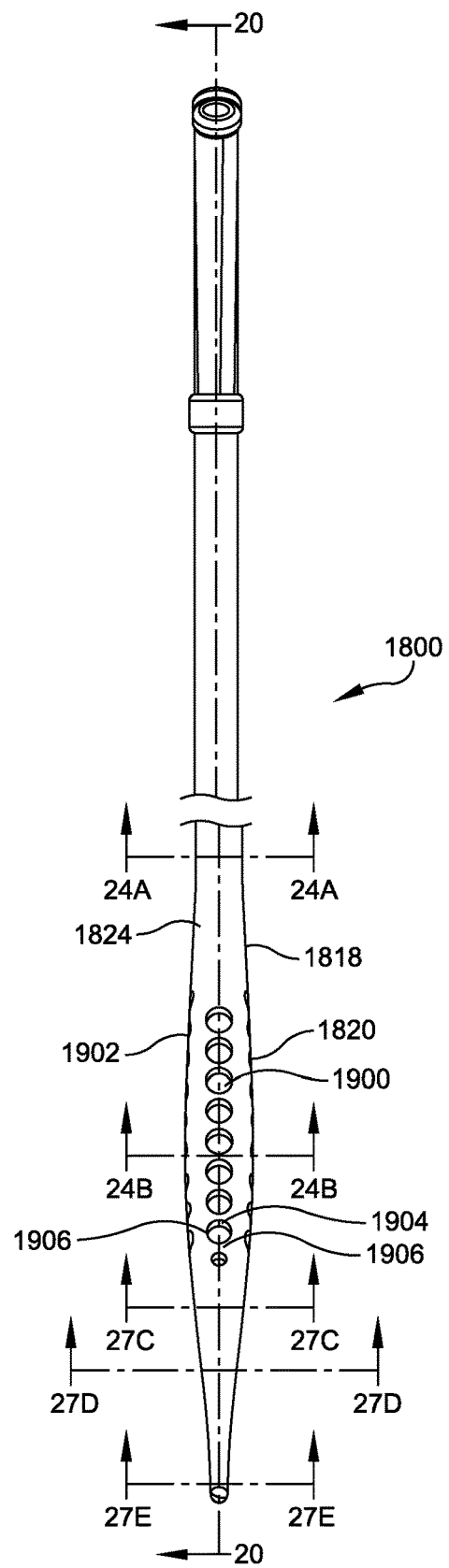
FIG. 19 is a partial left side elevational view of the sleeve tube of FIG. 18.

With reference now to FIG. 19, the distal section 1818 of the two-channel sleeve tube 1800 has a second curved row of flexion reliefs 1900 penetrating the periphery 1824 of the distal section 1818 transverse to the first curved row of eight flexion reliefs 1820 to allow the distal section 1818 to more easily bend at the location of the second row of flexion reliefs 1900 by collapsing the laterally opposed sides, e.g., 1904, 1906, of the flexion reliefs, e.g., 1908, towards each other. This distal section 1818 further includes a third curved row of nine flexion reliefs 1902 opposite the first curved row of flexion reliefs 1820 and transverse to the second row of flexion reliefs 1900, which provide a bending function in the same way as recited above for the other two rows of flexion reliefs 1820, 1900 except the direction of such bending is opposite that provided by the first row of flexion reliefs 1820.

Figure 20:
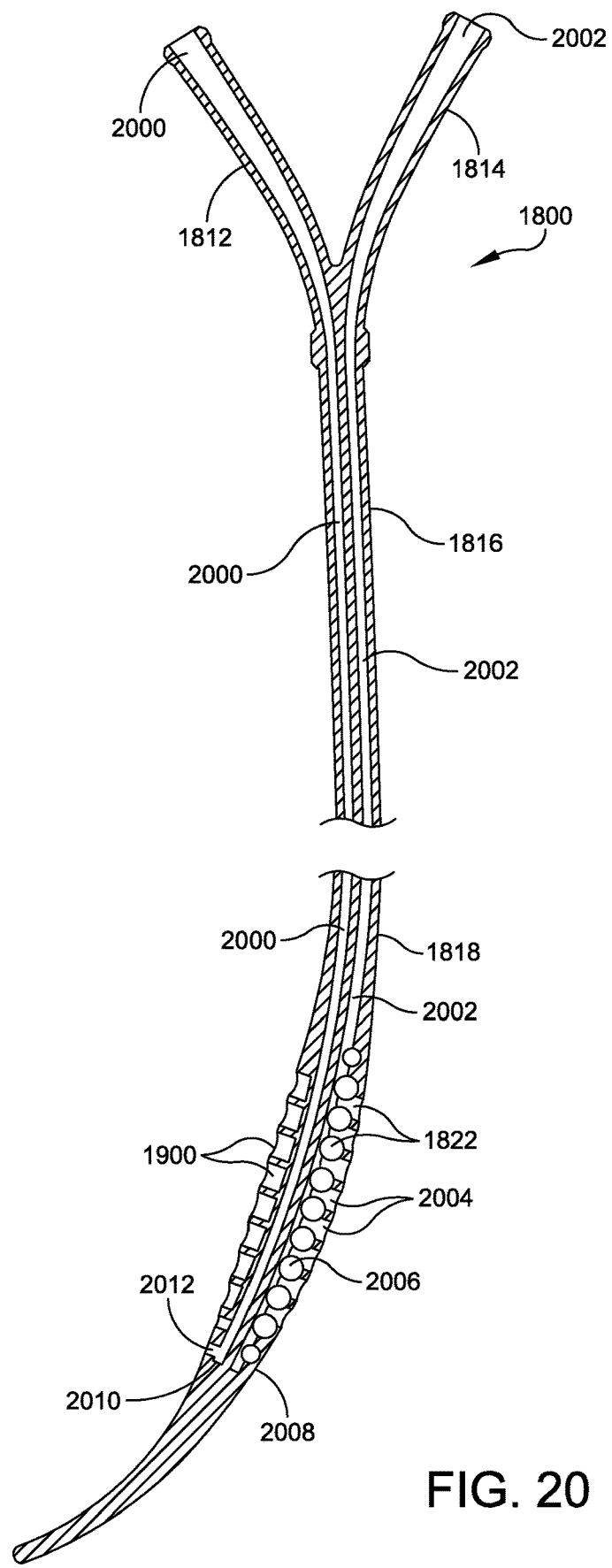
FIG. 20 is a partial cross-sectional view taken along section line 20-20 of FIG. 19.

Referring now to FIG. 20, an interior sump channel 2000 extends through the lateral length of the sump conduit 1812, through the lateral length of the main body section 1816, and through, and terminating at the lower end 2008 of, a substantial portion of the lateral length of the distal section 1818. Similarly, an interior suction channel 2002 also extends through the lateral length of the suction conduit 1814, through the lateral length of the main body section 1816, and through, and terminating at the lower end 2008 of, a substantial portion of the lateral length of the distal section 1818.

Each aperture among the first row of suction apertures 1822 is in material transfer communication with the interior suction channel 2002. Similarly and with reference to FIG. 21, a second row of suction apertures 2100 penetrates the opposing side 2102 of the distal section 1818, with each such opposing second row suction aperture, e.g., 2104, being (i) coaxial with an opposed suction aperture, e.g.,

2108, in the first row of suction apertures 1822 and (ii) in material transfer communication with the interior sump channel 2002 as well.

In contrast and with reference back to FIG. 20, the interior sump channel 2002 terminates at its lower end 2010 in a tubular sump vent 2012. The sump vent 2012 is transverse to the laterally extending axis of the interior sump channel 2002 at its lower end 2010 and is in material transfer communication with the interior sump channel 2002.

Figure 21:
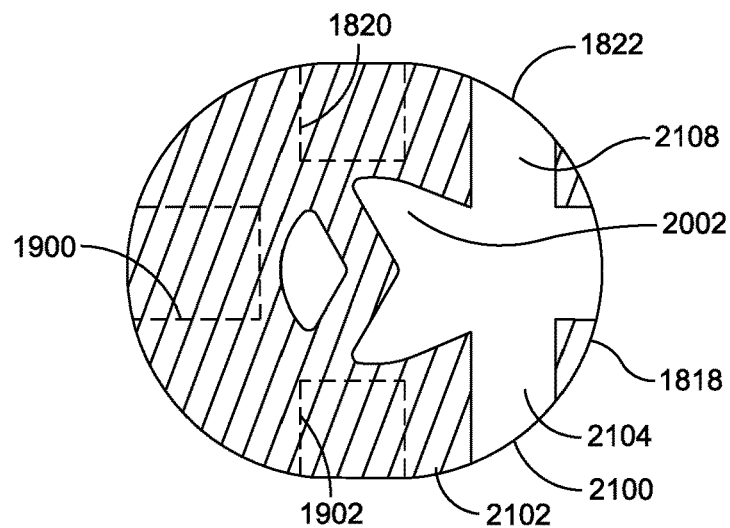
FIG. 21 is a cross-sectional view taken along section line 21-21 of FIG. 18.
Figure 22:
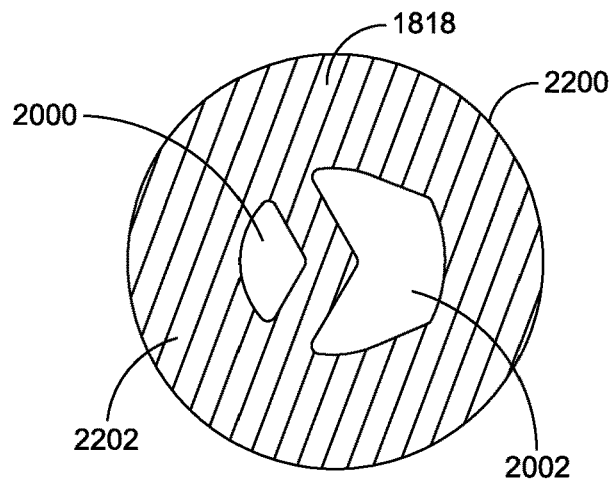
FIG. 22 is a cross-sectional view taken along section line 22-22 of FIG. 18.
Figure 23:
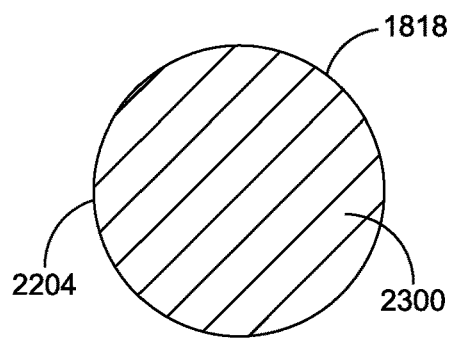
FIG. 23 is a cross-sectional view taken along section line 23-23 of FIG. 18.
Figure 24A:
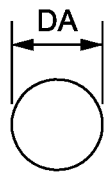
FIGS. 24 A, B, C, D, and E show the shape of the outer periphery of the sleeve tube at periphery cross-section lines 27 A-A, B-B, C-C, D-D, and E-E, respectively, of FIG. 19.
Figure 24B:
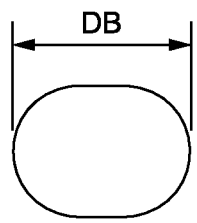
Figure 24C:
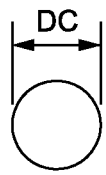
Figure 24D:
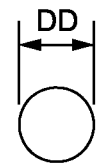
Figure 24E:
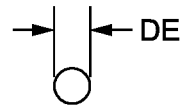

With reference now to FIGS. 18 and 22, the upper portion 2200 of the distal section 1818 intermediate, and extending between, the main body section 1816 and the rows of flexion reliefs, e.g., 1820, and suction apertures, e.g., 1822, has an outer somewhat tubular section 2202, with a circular or round outer periphery in cross-section (as also shown in FIG. 24A), surrounding the interior sump channel 2000 and adjacent interior suction channel 2002. Referring to FIGS. 18 and 23, the narrowed lower or tip portion 2204 of the distal section 1818 intermediate, and extending between, the distal tip end 1804 of the distal section 1818 and the rows of flexion reliefs, e.g., 1820, and suction apertures, e.g., 1822, is solid throughout its cross-section 2300. Referring to FIGS. 18 and 21, the central portion of the distal section 1818 at section line 21-21 has an oblong outer periphery in cross-section (explained further in association with FIG. 24B below).

With reference to FIGS. 19 and 24A-E, exemplary diameters of the distal section 1818 along its lateral length are: DA, at section line 24A-24A, 13.3 mm; DC, at section line 24C-24C, 13.3 mm; DD, at section line 24D-24D, 11 mm; and DE, at section line 24E-24E, 5 mm. The obround outer periphery DB of distal section 1818 at section line 24B-24B, has a narrower section maximum width of 19.2 mm and a wider section maximum width of 23.2 mm. Thus, the thickness of this distal section 1818 changes along its axial length, first thickening toward, and to provide, the rows of flexion reliefs, e.g., 1820, and then tapering to a relatively narrow, solid frusto-conical section adjacent, and terminating in, the distal tip end 1804.

In some embodiments, the distal section 1818 is made of material having 60-90 ShoreA durometer (hardness). In others, material having 75-85 ShoreA durometer can be more resilient while being sufficiently flexible. One exemplary distal section consists of mineral filled (for imaging opacity) thermoplastic rubber (TPR) or thermoplastice silicone rubber having 80 Shore A durometer.

In other embodiments, differing materials may be used and/or a removable stiffening element may be introduced into the tube, such as a rubber stiffener rod removably mountable into the suction channel. This stiffening element can be inserted within the suction channel before and during insertion into the patient and then removed in order to perform a procedure with the sleeve tube while inside the patient.

Figure 25:
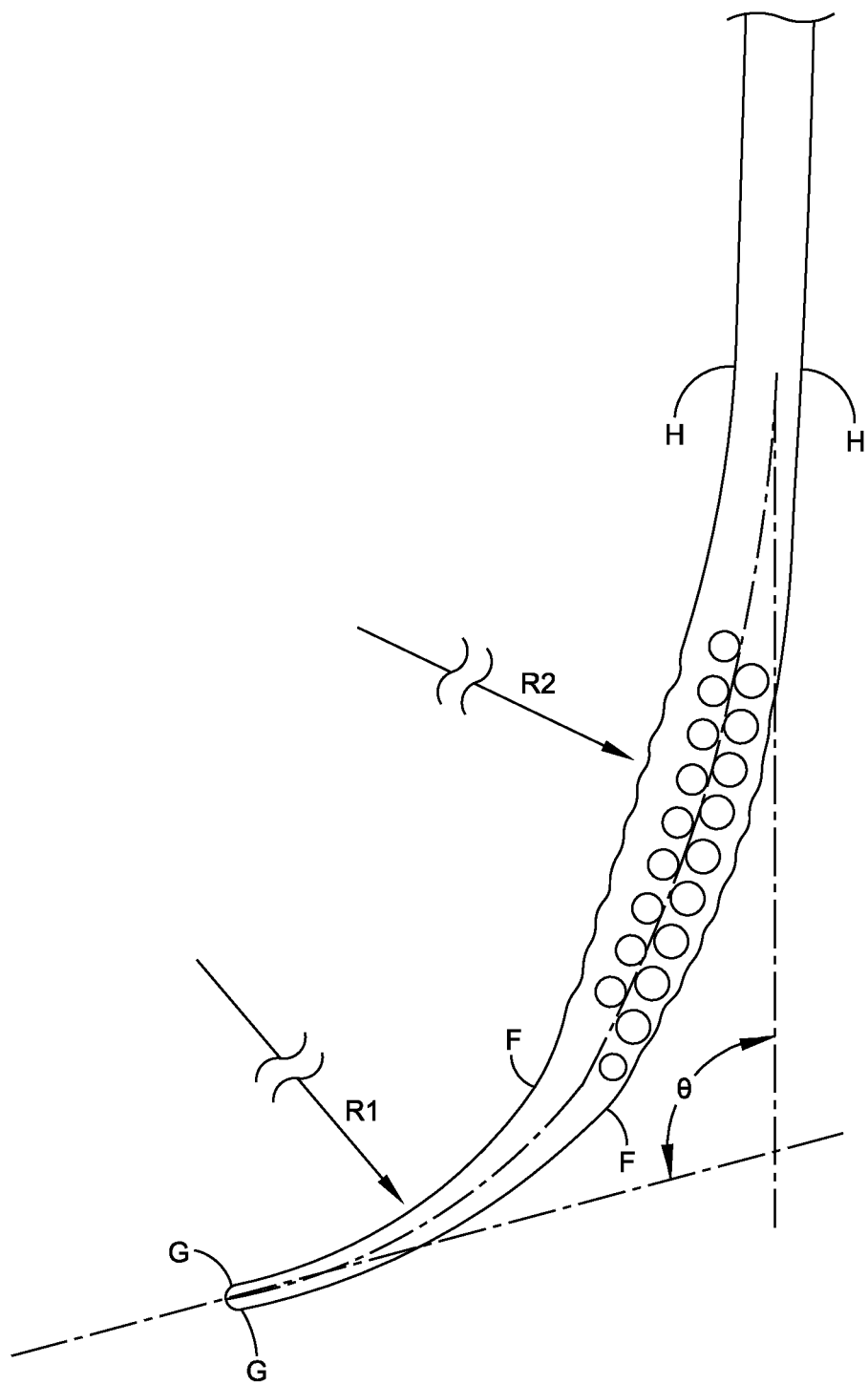
FIG. 25 is a front elevational view of the curved distal section of the sleeve tube of FIG. 18.

With reference now to FIG. 25, in one embodiment, the curved tip portion 2204 of the distal section 1818 between location lines F-F and G-G has a radius R1 and a radius R2 of the curved mid-portion of the distal section 1818 between location lines FF and HH. Some applications provide a curved tip portion 2204 that is tapered or frustoconical and has a predetermined curvature radius R1 that can conform to the esophageal anatomy and thus reduce the risk of esophageal perforation upon insertion.

In un-curved straight tubes of the prior art, there is often a point of resistance when inserting the tube into the stomach due in part to the sub diaphragmatic fat pad, and also due to the natural curvature of the stomach upon entry into it. Insertion of a straight tube can require substantial force, and hence cause trauma, in order to push the tube into the stomach.

In contrast, the sleeve tube of FIG. 25, for example, can provide the flexible but resilient curved tip portion 2204 having curvature such as R1, that can require less force and associated trauma when inserted into the patient's stomach. The tapered tip portion 2204 can allow safer passage through the upper esophagus and the lower esophagus, where natural muscles may narrow the esophageal lumen. In the upper esophagus, the cricopharyngeus muscles narrow the esophagus, and in the lower esophagus the lower esophageal sphincter muscles narrow the esophagus. Furthermore, the entry into the stomach from the lower esophagus involves a natural curve anteriorly—toward the front—of a human, due to natural anatomic curvature and the presence of the retroesophageal fat pad that lies posterior to the distal esophagus. The features of tapering, softness, pliability, and predetermined curvature of the tip portion 2204 can reduce the risk of esophageal perforation by facilitating smoother advancement of the tube into the stomach when compared to existing art. In this regard, in some embodiments, the tip portion 2204 of the distal section 1818 may be made of a soft material such as having ShoreA durometer within the range of 30-65, such as 50 for example.

In one embodiment, the curved lower portion radius R1 is 107.5 mm, whereas the upper curved portion radius R2 is 337 mm. The overall lower or ventral curvature angle $\Theta$ of the distal end section 1818 (i.e., at the intersection of the axis A-A of the main body section with the axis B-B of the distal section's tip end 1804) is 105 degrees; and R2 is determined in order to yield the predetermined overall ventral curvature angle $\Theta$ based on curved tip radius R1.

Figure 26:
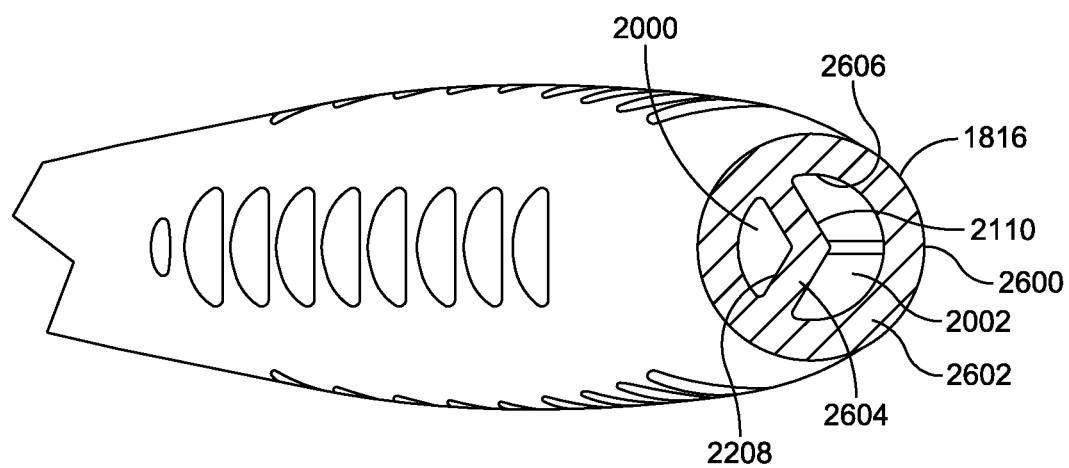
FIG. 26 is a cross-sectional view taken along section line 26-26 of FIG. 18.

With reference now to FIG. 26, the main body section 1816 has an outer tube 2602 with a V-shaped dividing wall 2604 spanning across the interior sidewall 2606 of the outer tube 2602. The dividing wall 2604 thus separates the interior of the outer tube 2602 to provide the interior sump channel 2000 and interior suction channel 2002 on opposed sides 2608, 2610, respectively, of the dividing wall 2604 within the outer tube 2602. The dividing wall 2604 can also stiffen the main body section 1816. In one embodiment, the diameter of the outer tube 2602 is 13.3 mm and is made from material similar to that of the distal end section. Similarly, the sump and suction tubular conduits 1812, 1814 shown in FIG. 28 may be made of the same type of material or differing material that may better transmit negative or positive pressures without collapsing or inflating. Thus, embodiments of the present sleeve tube may be made of materials that are recyclable, including if desired for re-use in subsequent surgeries involving differing patients.

Figure 27:
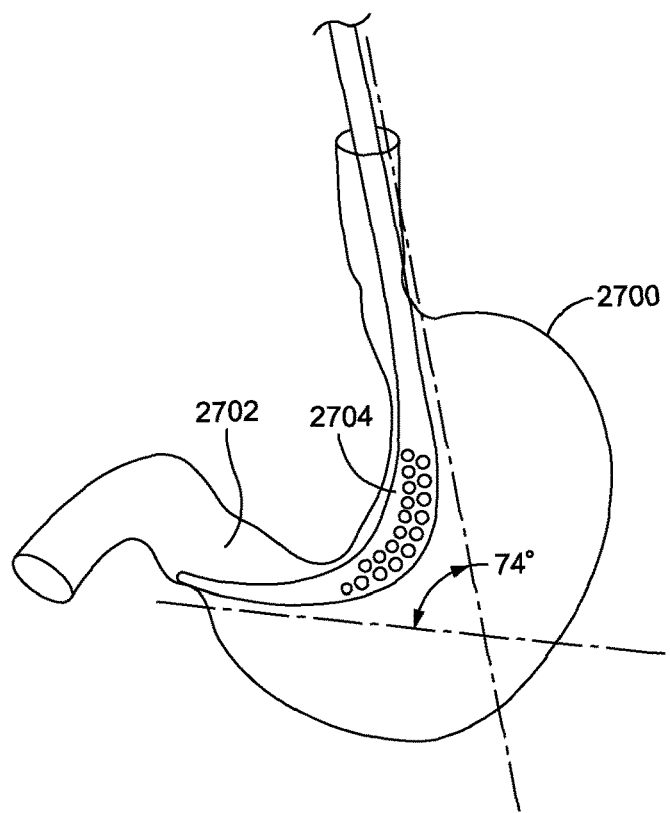
FIG. 27 is a partial cross-sectional view of one configuration of a human stomach with a sleeve tube having a sharply curved distal end penetrating the stomach.
Figure 28:
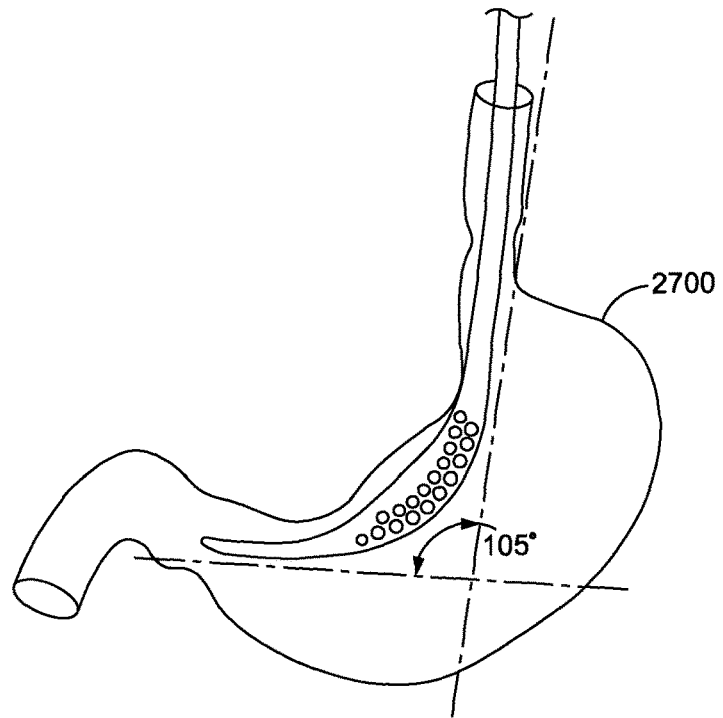
FIG. 28 is a partial cross-sectional view of a second configuration of a human stomach with a sleeve tube having a less sharply curved distal end penetrating the stomach.
Figure 29:
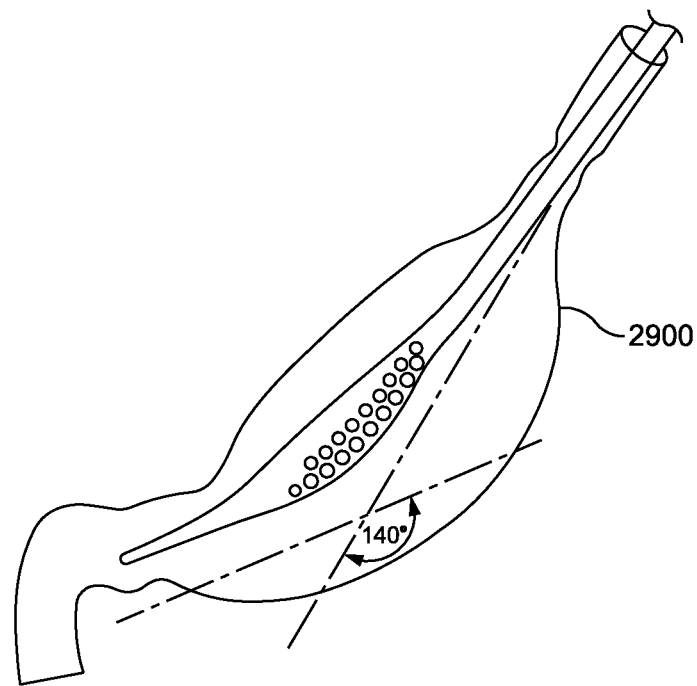
FIG. 29 is a partial cross-sectional view of a third configuration of a human stomach with a sleeve tube having an even less sharply curved distal end penetrating the stomach.

As shown in FIGS. 27, 28, and 29, the human stomach, e.g., 2700 in FIG. 7, has a natural reverse "C-shape" when viewed from the front of a person, with the reverse C-shape varying among differing people. In measurements of the acuity of the reverse C-shape among humans undergoing sleeve gastrectomy procedures, a useful analysis imagines a straight tube passing from the gastroesophageal junction, then turning within the body of the stomach to then enter the antrum of the stomach. Applicant has observed that one can measure the acuity of the reverse C-shaped curve by examining the position of entry through the gastroesophageal junction into the body of the stomach, and compare this position to the position required to advance from the body of the stomach into the antrum. In the applicant's experience, the degree to which a tube must turn to pass from the gastroesophageal junction fully into the antrum (the "gastroesphogael-to-antrum angle) measures, on average, 105 degrees as shown in FIG. 28.

In the applicant's experience, the gastroesphogael-to-antrum angle also can vary in differing people from 70 degrees to 145 degrees. For example: with reference to FIG. 27, this angle in a second exemplary stomach is approximately 74 degrees; and with reference to FIG. 29, this angle in a third exemplary stomach is 140 degrees.

Figure 30:
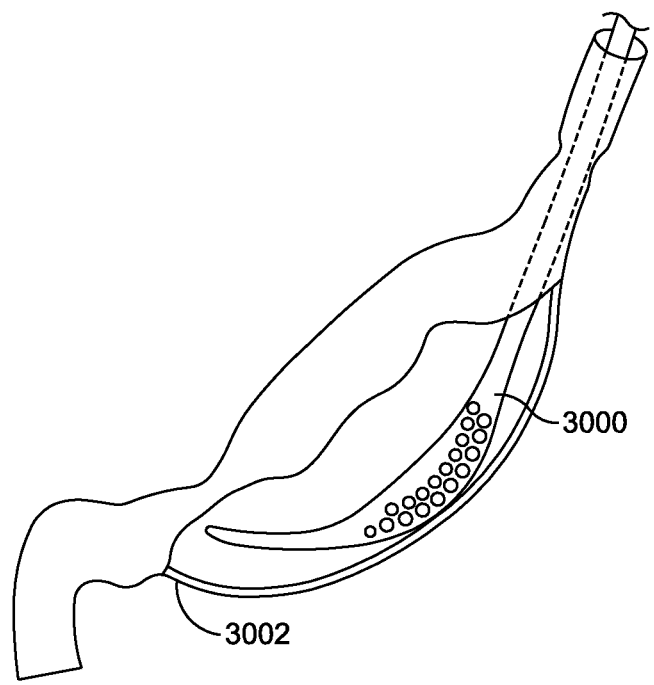
FIG. 30 is a partial cross-sectional view of a human stomach with an embodiment of the sleeve tube inserted so that the curved end abuts a lower end of the stomach.
Figure 32:
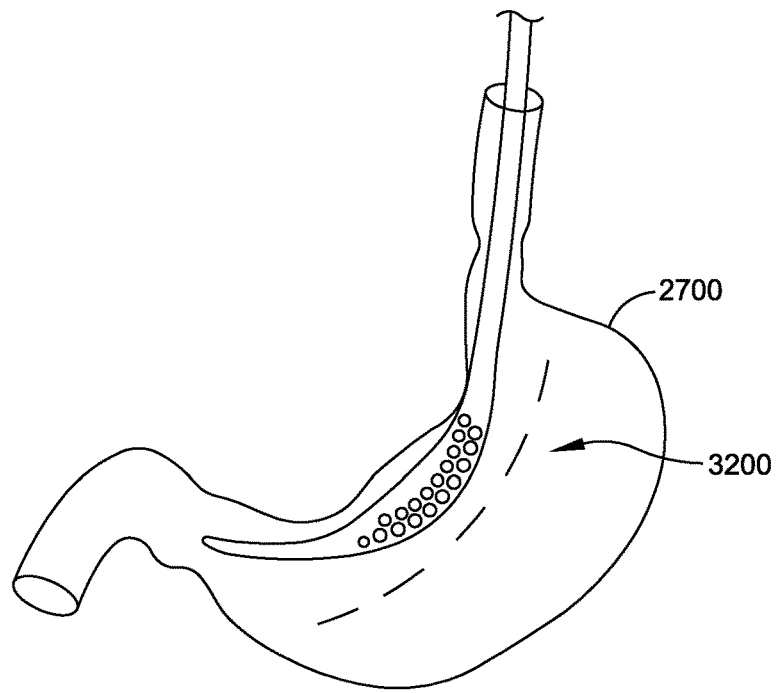
FIG. 32 is a partial cross-sectional view of the human stomach of FIG. 28 with the less sharply curved end of the sleeve tube being used during surgery to help calibrate the location of stapling of the stomach.

With reference back to FIG. 25, the applicant has discovered that the curvature angle $\Theta$ of the overall curvature of the distal section 1818 can be based upon the gastroesphogael-to-antrum angle and that such a curvature angle $\Theta$ of 105 degrees can be beneficial in facilitating an effective and safe adult gastric surgery generally. When such a sleeve tube is positioned into the antrum, it conforms to the natural human stomach anatomic shape and thus provides for a more natural calibration device that leads to less distortion of the stomach during surgery than a straight calibration tube would provide. The reduced distortion of the natural reverse C-shaped curvature of the stomach reduces distortion of the stomach anatomy during and after surgery is completed and thus reduces complications of stenosis and obstruction of the stomach postoperatively. Thus, the distal section 1818 shown in FIG. 30 is designed to provide a particular curvature angle $\Theta$ to the stomach antrum of, as shown in FIG. 28, 105 degrees. This particular curvature angle of 105 degrees can, however, be used on a wide variety of stomach angles and curvatures commonly incurred when using the sleeve tube on a variety of different patients. As shown in FIG. 32, this curvature can also provide a surgical calibration guide for stapling of the stomach along the dashed sapling line 3200

Figure 31:
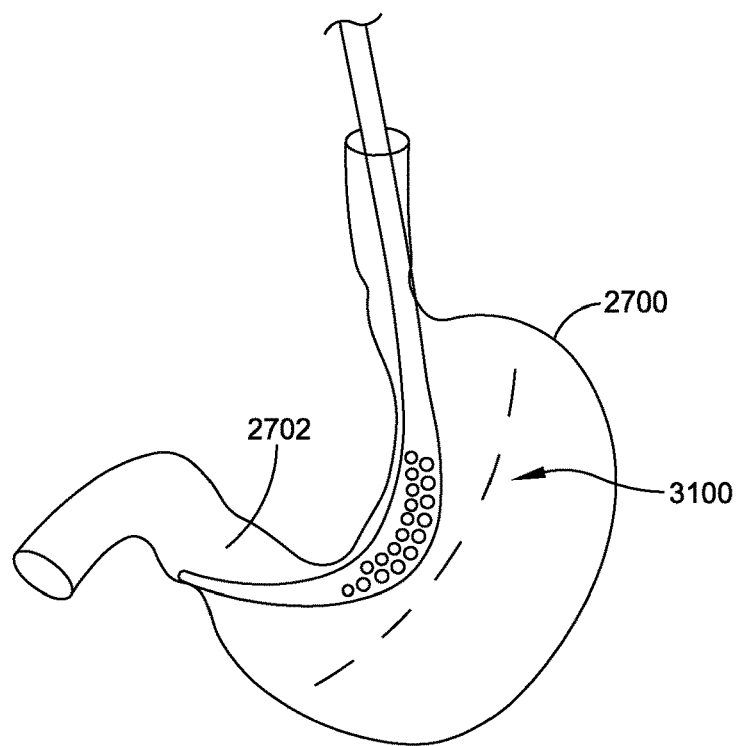
FIG. 31 is a partial cross-sectional view of the first human stomach of FIG. 27 with the sharply curved end of the sleeve tube being used during surgery to help calibrate the location of stapling of the stomach.
Figure 33:
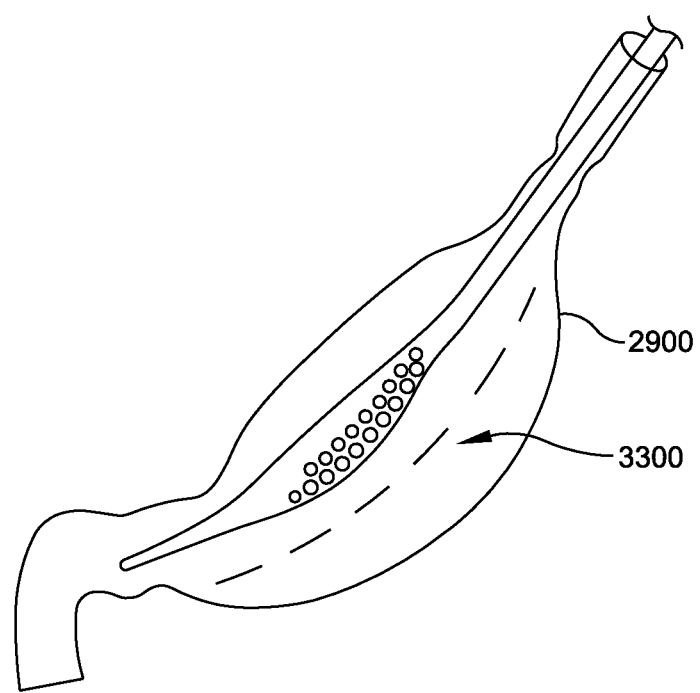
FIG. 33 is a partial cross-sectional view of the human stomach of FIG. 29 with the even less sharply curved end of the sleeve tube being used during surgery to help calibrate the location of stapling of the stomach.

The curvature angle $\Theta$ may be different. For example, the curvature angle $\Theta$ may be customized for a given patient or group of types of patients, so that a variety of differently structured sleeve tubes may be provided to provide differing structures for differing patients or types of patients. Thus, as shown in FIGS. 29 and 33 as an example, the angle $\Theta$ for an alternatively curved distal end section 2900 is 140 degrees to conform to an entry angle to the stomach antrum of, as shown in FIG. 29, 140 degrees and to also provide, as shown in FIG. 33, a surgical calibration guide for stapling of the stomach along the dashed sapling line 3300. Similarly, as shown in FIGS. 27 and 31 as another example, the angle $\Theta$ for an alternatively curved distal end section 2704 is 74 degrees to conform to an entry angle to the stomach antrum of, as shown in FIG. 27, 74 degrees and to also provide, as shown in FIG. 31, a surgical calibration guide for stapling of the stomach along the dashed sapling line 3100.

The distal end section may be removably mountable to the main body section so that differently-shaped distal end sections may be manufactured, stored, and then selected by the physician, mounted to the sleeve tube's main body section for use in a procedure with a patient, and later, if desire, removed from the main body section. With reference back to FIG. 18, the distal end section 1818 may be removably mounted to the main body section 1816 at junction 1834, or alternatively distal section 1818 may be secured to the main body section 1816 by adhesive or an adhering process fusing the distal section 1818 to the main body section 1816.

Figure 35:
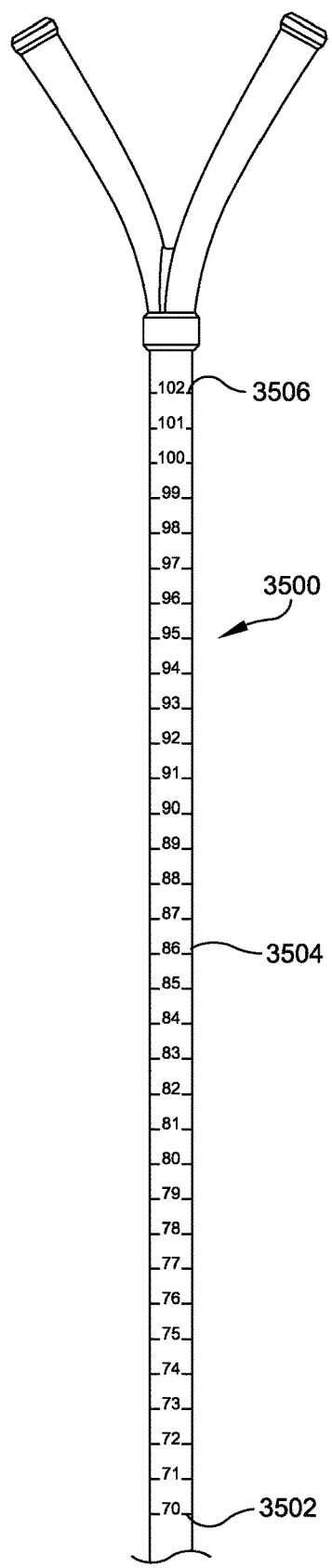
FIG. 35 is partial plan view of a sleeve tube having tube insertion calibration markings on the outer periphery of the sleeve tube.

With reference now to FIG. 35, some embodiments of the sleeve tubes of this application may have surgical guide or calibration markings, e.g., 3500. In the embodiment shown in FIG. 35, the calibration markings are in centimeters, commencing with 70 cm at the lower end 3502 of the calibration scale 3504 and ending at 102 cm at the upper end 3506 of the scale 3504. Thus, each calibration marking, e.g., 3502, indicates the distance from the marking to the sleeve tube's distal tip (not shown in FIG. 35); and these markings 3500 can be used in surgery to inform the surgeon of the length of the sleeve tube penetrating the patient's mouth, esophagus, and stomach as applicable.

Some embodiments of the two channel device can eliminate a manufacturing challenge, and associated cost and complexity, for inclusion of a third channel and balloon feature as in at least some of the embodiments of FIGS. 1-17. For example, the inclusion of the balloon and the third channel can, in some embodiments, involve additional and different materials which would not be required in the depicted two channel device. The two channel embodiment retains the suction channel for evacuation of gastric contents and facilitation of a dye pressure test by injecting dye through the sump channel.

Additionally, at least some two channel embodiments can provide the advantage of simplicity of use for the physician placing and advancing and positioning the tube. By creating the tube with an intrinsic expanded diameter at the location commonly corresponding to the gastric incisura, the tube functions to correspond to the gastric anatomy and facilitate completion of the sleeve gastrectomy surgical procedure while not requiring the added time to inflate a balloon. During surgery, and often at this early phase of the induction of general anesthesia and initiation of the anesthetic and surgical procedure, the two channel embodiment can, in at least some embodiments, allow the physician to reduce the amount of time positioning the tube within the patient. This can also allow for improved safety and monitoring of the anesthetic process and reduced time under anesthesia by the patient. Similarly, at least some two channel embodiments can be simpler to handle, less cumbersome to use, and less likely to result in an error of confusing the hubs or tube access channels. Further, at least some two-channel embodiments can be easier to store, package, and transport due to less mass and less additional packaging required to accommodate at least some three channel embodiments.

Figure 34:
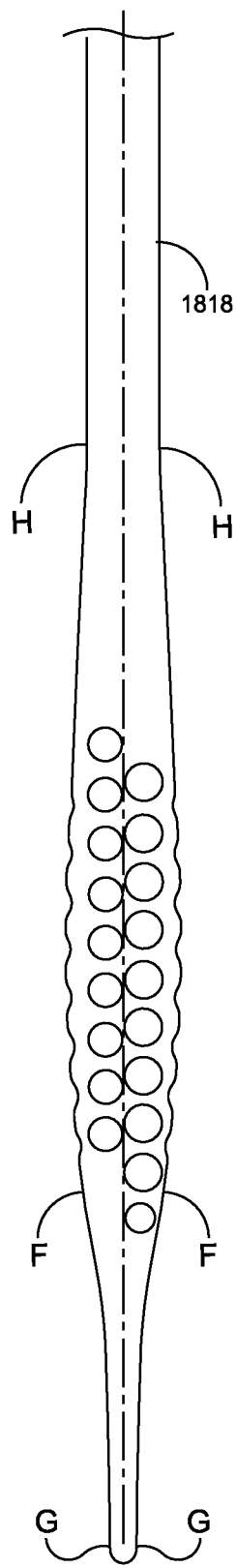
FIG. 34 is a partial elevational view of the distal section of the sleeve tube of FIG. 18 straightened as it moves through a patient's esophagus.

In one embodiment of the method of use of the depicted two channel embodiment of FIG. 18, the method of use of the two channel embodiment is much like the method of use of the three channel embodiment explained above, except there is no balloon or balloon inflation or deflations steps. Rather, as the distal end enters the esophagus, the distal section tube straightens as shown in FIG. 34, with the main body section then bending in the patient's mouth as the main section enters the esophagus. Thus, as the distal end passes through the esophagus and into the stomach, the sleeve tube bends and straightens to pass through different portions of the human body. For example, the tube straightens and bends to make a passage into the stomach adjacent the incisura area of the stomach. In some embodiments, the initial insertion, with curved distal section of the sleeve tube oriented to curve anteriorly (from the back side of the patient toward the front side of the patient), will enter the stomach more easily than any pre-existing art, by causing the tip end of the curved distal section to slide up and over the natural retro-esophageal fat pad in the stomach. Then the inserting physician can rotate the sleeve tube and its distal end section to the patient's right 90° (i.e., so that the curved distal end section curves toward the patient's pyloric antrum), following the natural reverse C-shape described above, while advancing them further and placing the distal section so that it curves generally along the natural stomach curvature to the right in the human stomach at the antrum as shown in FIGS. 31, 32, and 33. Even if the sleeve tube is inserted too far into the stomach as shown in FIG. 30, the curved end 3000 of the sleeve tub can abut the lower curved end 3002 of the stomach with less likelihood of causing trauma to the stomach.

Subsequently, when the sleeve tube is removed from the patient, the tube similarly bends and straightens, and can be rotated in reverse as compared to the insertion technique, to adjust to the inner curvatures and passages of the human body, making removal quick, easy, and less traumatic to the patient. Alternatively, at least some embodiments of this embodiment provide a sleeve tube that is sufficiently soft and pliable to allow a physician to simply pull the sleeve tube straight out of the patient, with no or little rotation, making removal even easier and quicker.

As compared to the prior art, this structure can thus make the distal section in particular easier to insert into the patient's mouth, esophagus, and stomach while also reducing the risk of causing edema to the patient during sleeve tube insertion, manipulation within the patient, and withdrawal from the patient. In addition, when the distal section is inserted into the stomach the diameter of the tube's distal section is significantly greater at the area of the incisura of the stomach. In some embodiments, this innovative feature enhances the safety of sleeve gastrectomy.

As noted above, the thickened portion of the distal section can provide calibration of the residual stomach sleeve by causing the surgeon's stapling device to provide a wider stomach sleeve to help prevent folding, stenosis, increased intraluminal pressure, and leaks of the residual stomach. In other words, without the widened distal section diameter at this location when adjacent the incisura of the stomach, the sleeve gastrectomy procedure can create a risk of stenosis or obstruction due to the combined effects of a narrowed stomach sleeve at or near the point of maximum angulation of the stomach. Because this location of the incisura is at or near the point of maximum angulation and potential point of folding or twisting the stomach, the standard diameters of prior art uniform calibration tubes typically do not adequately protect against stenosis.

As the sleeve tube insertion or withdrawal takes place, calibration or length markings on the sleeve tube can be used to identify the length of the sleeve tube inserted into the patient. Monitoring the length of insertion can help the surgeon also identify the location of the distal curved section of the tube during the insertion and withdrawal procedures.

All dimensions and angles disclosed above can be varied for varying circumstances, uses, and objects. They may be varied by ranges of plus or minus 1% through up to 40% with the ranges in some embodiments varying by differing amounts for differing aspects of a given sleeve tube and sleeve tube application. Further, the designs depicted in the Figures, especially the two channel embodiment, are directed to use in humans. The designs may be varied for other applications of course.

The process parameters, functions, system features, and sequence of steps described and/or illustrated herein are given by way of example only and may be varied and mixed and matched as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The foregoing detailed description has described some specific embodiments. However, the illustrative discussions above are not intended to be exhaustive or to limit the invention to the precise forms disclosed. Many modifications and variations are possible in view of the above teachings. The embodiments were chosen and described in order to explain the principles of the present systems and methods and their practical applications, to thereby enable others skilled in the art to best utilize the present systems, their components, and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon." Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C).

Unless otherwise indicated, all numbers or expressions, such as those expressing dimensions, physical characteristics, and the like, used in the specification (other than the claims) are understood to be modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

All disclosed numerical values are to be understood as being variable from within minus 90% to plus 100% and thus provide support for claims that recite such values or any and all ranges or subranges that can be formed by such values. For example, a stated numerical value of 8 should be understood to be capable of varying from 0.8 (minus 90%) to 16 (plus 100%). The subject matter recited in the claims is not coextensive with and should not be interpreted to be coextensive with any embodiment, feature, or combination of features described or illustrated in this document. This is true even if only a single embodiment of the feature or combination of features is illustrated and described in this document.

What we claim is:
1. An orogastric tube comprising:
a proximal end section;
a distal working end section opposite the proximal end section, the distal working end section having a preformed, predetermined, flexible, and resilient curved working portion having a predetermined overall ventral curvature angle of 70-145 degrees;

a main body section intermediate the proximal end section and distal working end section;

a sump channel extending from the proximal end section, through the main body section, and into the curved working end section;

a suction channel extending from the proximal end section, through the main body section, and into the curved working end section;

the distal working end section having a tubular outer wall surrounding (i) the sump channel section within the distal working end section and (ii) the suction channel section within the distal working end;

wherein the curved working portion of the distal working end section includes a preformed, predetermined curved row of flexion reliefs penetrating an outer wall of the curved working portion, wherein said flexion reliefs are configured to allow the outer wall of the curved working portion to bend at a location of said flexion reliefs;

the curved working portion of the distal working end section having a preformed, predetermined curved first row of suction apertures penetrating the outer wall of the distal working end section and in material transfer communication with the suction channel, and (ii) a preformed, predetermined curved second row of suction apertures penetrating the outer wall of the distal working end section and in material transfer communication with the sump channel.

2. The orogastric tube of claim 1 wherein the curved working portion of the distal working end section is intermediate a preformed, predetermined resilient curved tip and the main body section.

3. The orogastric tube of claim 1 wherein the tubular outer wall of the distal working end section includes a curved working surgical calibration guide.

4. The orogastric tube of claim 1 wherein the tubular outer wall of the of the distal working end section includes a curved working surgical calibration guide.

5. The orogastric tube of claim 3 wherein each first row suction aperture in the curved first row of suction apertures is coaxial with a second row suction aperture in the curved second row of suction apertures.

6. The orogastric tube of claim 4 wherein each first row suction aperture in the curved first row of suction apertures is coaxial with a second row suction aperture in the curved second row of suction apertures.

7. The orogastric tube of claim 1 wherein the predetermined overall ventral curvature angle of the curved working portion is between 74 and 140 degrees.

8. The orogastric tube of claim 6 wherein the predetermined overall ventral curvature angle of the curved working portion is between 74 and 140 degrees.

9. The orogastric tube of claim 1 wherein the distal working end section has a thin-thicker-thin cross-section extending along a lateral length of the distal working end section.

10. The orogastric tube of claim 2 wherein the distal working end section has a thin-thicker-thin cross-section extending along a lateral length of the distal working end section.

11. The orogastric tube of claim 7 wherein the distal working end section has a thin-thicker-thin cross-section extending along a lateral length of the distal working end section.

12. The orogastric tube of claim 8 wherein the distal working end section has a thin-thicker-thin cross-section extending along its lateral length.

13. The orogastric tube of claim 2 wherein the curved working portion has a first section with a first radius of curvature and a second section with a second radius of curvature different from the first radius of curvature.

14. The orogastric tube of claim 8 wherein the curved working portion has a first section with a first radius of curvature and a second section with a second radius of curvature different from the first radius of curvature.

15. The orogastric tube of claim 1 wherein the main body section has an outer main body periphery with length calibration markings extending along the outer main body periphery.

16. The orogastric tube of claim 14 wherein the main body section has an outer main body periphery with length calibration markings extending along the outer main body periphery.

17. The orogastric tube of claim 1 wherein the tubular outer wall of the distal working end section includes a curved working surgical calibration guide.

18. The orogastric tube of claim 1 where the orogastric tube is a gastrectomy tube.

19. The orogastric tube of claim 2 where the orogastric tube is a gastrectomy tube.

20. The orogastric tube of claim 1 where the orogastric tube is a gastrectomy tube.

21. The orogastric tube of claim 7 where the orogastric tube is a gastrectomy tube.

22. The orogastric tube of claim 10 where the orogastric tube is a gastrectomy tube.

23. The orogastric tube of claim 16 where the orogastric tube is a gastrectomy tube.

* * * * *

UNITED STATES PATENT AND TRADEMARK OFFICE
CERTIFICATE OF CORRECTION

Page 1 of 1

PATENT NO. : 10,653,545 B2
APPLICATION NO. : 15/838057
DATED : May 19, 2020
INVENTOR(S) : Kent C. Sasse and Matthew T. Fisher It is certified that error appears in the above-identified patent and that said Letters Patent is hereby corrected as shown below:

In the Claims

Column 21 Line 22: Insert -- (i) -- between the word "having" and the word "a"

Signed and Sealed this
Eleventh Day of August, 2020

Andrei Iancu
*Director of the United States Patent and Trademark Office*